(12) United States Patent
Bonne

(10) Patent No.: US 7,779,671 B2
(45) Date of Patent: Aug. 24, 2010

(54) PHASED MICRO ANALYZER VIII

(75) Inventor: Ulrich Bonne, Hopkins, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 12/327,778

(22) Filed: Dec. 3, 2008

(65) Prior Publication Data

US 2009/0100906 A1    Apr. 23, 2009

Related U.S. Application Data

(60) Division of application No. 10/829,763, filed on Apr. 21, 2004, now Pat. No. 7,530,257, which is a continuation-in-part of application No. 10/672,483, filed on Sep. 26, 2003, now Pat. No. 7,367,216, application No. 12/327,778, which is a continuation-in-part of application No. 10/749,863, filed on Dec. 31, 2003, which is a continuation-in-part of application No. 10/672,483, and a continuation-in-part of application No. 10/671,930, filed on Sep. 26, 2003.

(60) Provisional application No. 60/500,821, filed on Sep. 4, 2003, provisional application No. 60/440,108, filed on Jan. 15, 2003, provisional application No. 60/414,211, filed on Sep. 27, 2002.

(51) Int. Cl.
    *G01N 25/00* (2006.01)
(52) U.S. Cl. .................................................. 73/25.01
(58) Field of Classification Search ................ 73/23.24, 73/23.25, 25.01, 31.05, 863.12
    See application file for complete search history.

(56) References Cited

U.S. PATENT DOCUMENTS 3,146,616 A    9/1964    Loyd (Continued)

FOREIGN PATENT DOCUMENTS

DE    2 934 566 A1    3/1981

(Continued)

OTHER PUBLICATIONS

Atalla et al., "Radiation Effects with the AC Heated Strip Technique for the Measurement of Thermal Properties of Liquids", *High Temperatures—High Pressures*, vol. 17, pp. 447-452, 1985.

(Continued)

*Primary Examiner*—John Fitzgerald
(74) *Attorney, Agent, or Firm*—Crompton Seager & Tufte LLC

(57) ABSTRACT

A micro fluid analyzer that may be highly sensitive, fast and very compact. The analyzer may use sufficiently low power per analysis to be easily implemented with an equivalently small battery pack or other portable power source. There may be energy conservation features in the analyzer, such as optimal adsorber film thicknesses in the pre-concentrator, concentrator and chromatographic separators. There may be special timing of the phased heating elements in the concentrators and separators to further reduce energy consumption. Various kinds of detectors and sensors may be incorporated in the analyzer for achieving low probability for false positives and detection versatility. There may be a controller that provides data acquisition and analyzes, drive signals for control, management of wireless signal transmission and reception, processing, and other operational uses of the micro analyzer.

9 Claims, 30 Drawing Sheets

U.S. PATENT DOCUMENTS

| | | |
|---|---|---|
| 3,557,532 A | 1/1971 | Broerman |
| 3,589,171 A | 6/1971 | Haley |
| 3,783,356 A | 1/1974 | Lide, III et al. |
| 3,925,022 A | 12/1975 | Showalter et al. |
| 4,043,196 A | 8/1977 | Trageser |
| 4,228,815 A | 10/1980 | Juffa et al. |
| 4,236,404 A | 12/1980 | Ketchum et al. |
| 4,324,566 A | 4/1982 | Jacob et al. |
| 4,402,211 A | 9/1983 | Sugawara et al. |
| 4,472,355 A | 9/1984 | Hickam et al. |
| 4,478,076 A | 10/1984 | Bohrer |
| 4,483,200 A | 11/1984 | Togawa et al. |
| 4,502,320 A | 3/1985 | Sakai et al. |
| 4,507,974 A | 4/1985 | Yelderman |
| 4,576,050 A | 3/1986 | Lambert |
| 4,735,082 A | 4/1988 | Kolloff |
| 4,759,210 A | 7/1988 | Wohltjen |
| 4,778,764 A | 10/1988 | Fine |
| 4,805,441 A | 2/1989 | Sides et al. |
| 4,909,078 A | 3/1990 | Sittler et al. |
| 4,923,486 A | 5/1990 | Rubey |
| 4,944,035 A | 7/1990 | Aagardl et al. |
| 5,031,126 A | 7/1991 | McCulloch et al. |
| 5,044,766 A | 9/1991 | Stuart |
| 5,056,047 A | 10/1991 | Sondergeld |
| 5,092,218 A | 3/1992 | Fine et al. |
| 5,146,414 A | 9/1992 | McKown et al. |
| 5,168,746 A | 12/1992 | Madhusudhan et al. |
| 5,196,039 A | 3/1993 | Phillips et al. |
| 5,205,154 A | 4/1993 | Lee et al. |
| 5,243,858 A | 9/1993 | Erskine et al. |
| 5,263,380 A | 11/1993 | Sultan et al. |
| 5,268,302 A | 12/1993 | Rounbehler et al. |
| 5,268,303 A | 12/1993 | Bourne |
| 5,300,758 A | 4/1994 | Rounbehler et al. |
| 5,310,681 A | 5/1994 | Rounbehler et al. |
| 5,313,061 A | 5/1994 | Drew et al. |
| 5,379,630 A | 1/1995 | Lacey |
| 5,435,169 A | 7/1995 | Mitra |
| 5,442,175 A | 8/1995 | Dawson |
| 5,463,899 A | 11/1995 | Zemel et al. |
| 5,533,412 A | 7/1996 | Jerman et al. |
| 5,544,276 A | 8/1996 | Loux et al. |
| 5,551,278 A | 9/1996 | Rounbehler et al. |
| 5,552,042 A | 9/1996 | Le Febre et al. |
| 5,585,575 A | 12/1996 | Corrigan et al. |
| 5,587,520 A | 12/1996 | Rhodes |
| 5,591,321 A | 1/1997 | Pyke |
| 5,630,943 A | 5/1997 | Grill |
| 5,808,178 A | 9/1998 | Rounbehler et al. |
| 5,852,308 A | 12/1998 | Wood |
| 5,869,749 A | 2/1999 | Bonne et al. |
| 5,898,101 A | 4/1999 | Lyle et al. |
| 5,922,974 A | 7/1999 | Davison et al. |
| 5,970,803 A | 10/1999 | Staples et al. |
| 5,985,673 A | 11/1999 | Bao et al. |
| 6,016,027 A | 1/2000 | DeTemple et al. |
| 6,041,643 A | 3/2000 | Stokes et al. |
| 6,068,684 A | 5/2000 | Overton |
| 6,131,440 A | 10/2000 | Bertrand |
| 6,139,384 A | 10/2000 | DeTemple et al. |
| 6,155,097 A | 12/2000 | Arnold |
| 6,178,811 B1 | 1/2001 | Bonne et al. |
| 6,194,833 B1 | 2/2001 | DeTemple et al. |
| 6,217,829 B1 | 4/2001 | Mustacich et al. |
| 6,308,553 B1 | 10/2001 | Bonne et al. |
| 6,311,544 B1 | 11/2001 | Bertrand |
| 6,386,014 B1 | 5/2002 | Butch |
| 6,393,894 B1 | 5/2002 | Bonne et al. |
| 6,413,781 B1 | 7/2002 | Geis et al. |
| 6,494,617 B1 | 12/2002 | Stokes et al. |
| 6,497,138 B1 | 12/2002 | Abdel-Rahman et al. |
| 6,497,844 B1 | 12/2002 | Bacaud et al. |
| 6,527,835 B1 | 3/2003 | Manginell et al. |
| 6,610,977 B2 | 8/2003 | Megerle |
| 6,649,129 B1 | 11/2003 | Neal |
| 6,666,907 B1 | 12/2003 | Manginell et al. |
| 6,732,567 B2 | 5/2004 | Briscoe et al. |
| 6,792,794 B2 | 9/2004 | Bonne et al. |
| 6,837,096 B2 | 1/2005 | Stewart |
| 6,837,118 B2 | 1/2005 | Bonne et al. |
| 6,838,640 B2 | 1/2005 | Wise et al. |
| 6,914,220 B2 | 7/2005 | Tian et al. |
| 7,000,452 B2 | 2/2006 | Bonne et al. |
| 7,074,327 B2 | 7/2006 | O'Connor et al. |
| 7,104,112 B2 | 9/2006 | Bonne |
| 2002/0124631 A1 | 9/2002 | Sunshine et al. |
| 2004/0043479 A1 | 3/2004 | Briscoe et al. |
| 2004/0060346 A1 | 4/2004 | Bonne et al. |
| 2004/0137637 A1 | 7/2004 | Wang et al. |
| 2005/0095722 A1 | 5/2005 | McGill et al. |

FOREIGN PATENT DOCUMENTS

| | | |
|---|---|---|
| DE | 32 34 146 A1 | 3/1984 |
| DE | 42 22 458 A1 | 1/1994 |
| DE | 42 43 573 A1 | 6/1994 |
| DE | 296 07 315 U1 | 9/1996 |
| DE | 196 19 133 A1 | 11/1997 |
| EP | 0 232 719 A1 | 1/1987 |
| EP | 0 348 245 A2 | 12/1989 |
| EP | 0 364 982 A2 | 4/1990 |
| EP | 0 419 873 A2 | 8/1990 |
| EP | 0 468 793 A2 | 1/1992 |
| EP | 0 702 212 A2 | 3/1996 |
| EP | 0 773 432 A2 | 5/1997 |
| GB | 2 287 792 A | 9/1995 |
| JP | 56-153256 | 11/1981 |
| JP | 57-131029 | 8/1982 |
| JP | 57-206830 | 12/1982 |
| WO | WO 92/06369 | 4/1992 |
| WO | WO 94/20825 | 9/1994 |
| WO | WO 98/22793 | 5/1998 |
| WO | WO 0079243 A1 | 12/2000 |

OTHER PUBLICATIONS

Atalla et al. "Measurement of Thermal Properties of Liquids with an AC Heated-Wire Technique", *Interational Journal of Thermophysics*, vol. 2, No. 2, 1981.

Bonne et al., "Industrial Wireless PHASED Sensor Phase 1. Feasibility Demonstration," Progress Report for 4th Quarter of 2002, pp. 1-17, Jan. 31, 2002.

Bonne, et al., "PHASED: a Faster, Smarter and More Affordable Gas Analysis Device," 16th International Forum on Process Analytical Chemistry, San Diego, CA., Jan. 22-25, 2002, pp. 1-17.

Bonne, U., et al., "New Gas Composition and Trace Contaminant Sensors," GTI Natural Gas Technologies Conference, Orland, FL, Sep. 30-Oct. 2, 2002, pp. 1-12.

Bonne, et al., "PHASED, a Faster, Smarter and More Affordable Gas Analysis Device—Update," International Forum on Process Analytical Chemistry (IFPAC) Scottsdale, AZ, Jan. 21-24, 2003.

Bonne, et al., "Actuation-based microsensors," Smart Materials and Structures, 10, pp. 1185-1195, 2001.

Bonne et al., "Micro Gas Chromatography Tradeoff Study Final Report," to DARPA-MTO, Honeywell Labs, pp. 1-50, Dec. 1, 2003.

Bonne, "PHASED Gas Analyzer," DARPA Micro Gas Analyzer Workshop, Monteredy, CA., 1 page, Dec. 16-17, 2002.

Cabuz, C. et al., "Mesoscopic Sampler Based on 3-DF Arrays of Electrostatically Actuated Diaphragms," Proc. 10th Conf. S.S. S&A. Transducers '99 Jun. 7-12, 1999, Sendai, Japan.

Cabuz, C., et al., "The Dual Diaphragm Pump," IEEE, pp. 519-522, 2001.

Dipl.-Ing. Dr. techn. Wolfgang Wehrmann et al., "Korrelationstechnik", *Expert Verlag*, Grafenau, XP002094984, 173 pages, 1980.

Fuggerth, Endre, "Zone Gas Chromatography," Analytical Chemistry, 61, No. 14, pp. 1478-1485, (1989).

Goschnick, J., "An electronic nose for intelligent consumer products based on a gas analytical gradient microarray," Microelectronic Engineering, 57-58 pp. 693-704, 2001.

Honeywell Electronic Materials Interconnect Solutions, Thin Films—Dielectrics, Comparison of Solution and Film Properties, Advanced Products for IC Fabrication, 1 page.

http://www.advanced-polymers.com/star_center/techincal_papers/reduction_in_effective_dielectric_constant.pdf, 1 page.

http://www.chrompack.com/cgi/applicsview?ap=A00607&Go=G0, NexTrieve document view, 2 pages, printed Dec. 26, 2002.

http://www.zoex.com/html/technote_kt030505-1.html, Zoex Corporation, "A New Window on the Che," 5 pages, printed Mar. 15, 2004.

http://www.darpa.mil/baa/baa03-40.htm, baa04-40, DARPA Defense Advanced Research Projects Ag, 6 pages, printed Oct. 6, 2004.

International Search Report, PCT/US00/19924, mailed Mar. 5, 2001, 7 pages.

Kenndler, Ernst, "Gas Chromatography," Institute for Analytical Chemistry, University of Vienna, pp. 1-34, Sep. 9, 1999.

Kindlund et al., "Quartz Crystal Gas Monitor With Gas Concentrating Stage," Sensors and Actuators, 6 (1984) pp. 1-17.

Park, et al., "Microdischarge Arrays: A New Family of Photonic Devices (Revised)," IEEE Journal on Selected Topics in Quantum Electronics, vol. 8, No. 2, pp. 387-394, Mar./Apr. 2002.

Park, et al., "Photodetection in the visible, ultraviolet, and near-infrared with silicon microdischarge devices," Applied Physics Letters, vol. 81, No. 24, pp. 4529-4531, Dec. 9, 2002.

Park, et al., : Arrays of silicon micro discharge devices with multicomponent dielectrics, Optics Letters, vol. 26, No. 22, pp. 1773-1775, Nov. 15, 2001.

Phillips, J.B. et al., "Thermal Modulation: A Chemical Instrumentation Component of Potential Value in Improving Portability," Field Analytical Chemistry and Technology, 1(1): 23-29, 1996.

Quimby, et al., "Evaluation of a Microwave Cavity, Discharge Tube, and Gas Flow System of Combined Aas Chromatography—Atomic Emission Detection," Analytical Chemistry, Vol. 62, No. 10, pp. 1027-1034, May 15, 1990.

Stevenson, Robert, "Wintergreen '97," The World of Separation Science, The 19th International Symposium on Capillary Chromatography and Electrophoresis, 11 pages.

Toker et al., "Design and development of a fiber optic TDI CCD-based slot-scan digital mammography system," X-ray Detector Physics and Applications II, Proceedings SPIE-The International Society for Optical Engineering, vol. 2009 (Jul. 13-14, 1993) pp. 246-252.

Whitman et al., "Double-Injection FIA Using First-Order Calibration for Multicomponent Analysis," Analytical Chemistry 63 (1991) pp. 775-781.

Comparison of Detection Limits in pg/s (MDL) and Selectivities x $10^3$ (SEL)

| element | wavelength, nm | Present work | | Ref C (without background correction) | | Ref C (with background correction) | | Ref A (echelle) | | Ref B (with background correction) | |
|---|---|---|---|---|---|---|---|---|---|---|---|
| | | MDL | SEL | MDL | SEL | MDL | SEL | MDL | SEL | MDL | SEL |
| N | 174.2 | 7.0 | 6 | | | | | | | | |
| S | 180.7 | 1.7 | 150 | | | | | | | | |
| Hg | 184.9 | 0.1 | 3000 | | | | | | | 53 | |
| C | 193.1 | 0.5 | | | | | | | | | |
| F | 177.5 | 1.5 | 25 | | | | | | | | |
| C | 247.9 | 2.6 | | 2.7 | | | | | | | |
| Si | 251.6 | 7.6 | 90 | 9.3 | 1.6 | | | 58 | 3.9 | | |
| P | 253.6 | | | 3.3 | 11 | | | 4.2 | 26 | | |
| Hg | 253.7 | 0.1 | 5000 | 0.6 | 77 | | | 2.0 | 91 | | |
| Br | 470.4 | | | 33 | 0.27 | 67 | 1.0 | 20 | 1.4 | 38 | 0.53 |
| Br | 478.6 | 76 | 19 | 34 | 0.60 | | | | | | |
| Cl | 479.5 | 39 | 25 | 43 | 0.61 | 86 | 1.5 | | | 32 | 1.0 |
| Cl | 481.0 | | | | | | | 32 | 2.4 | | |
| H | 486.1 | 2.2 | | 16 | | | | | | | |
| S | 545.4 | 7.2 | 26 | 33 | 0.08 | 52 | 4.6 | 126 | 0.25 | 234 | 0.07 |
| D | 656.1 | 2.5 | 0.6$^c$ | 7.4 | 0.19 | | | | | | |
| H | 656.3 | 3.0 | | 7.5 | | | | | | 37 | |
| F | 685.6 | 40 | 30 | 20 | 0.57 | 180 | 11.4 | 17 | 3.5 | 11 | 0.82 |
| O | 777.2 | 76 | 25 | | | | | | | | |

Reference A uses peak width at base instead of peak width at half height to determine MDL, and the numbers have been adjusted accordingly for comparison. Reference B uses 1σ instead of peak to peak (6σ) to measure noise for MDL, and their numbers have been adjusted accordingly for comparison. $^c$Versus hydrogen.

*Figure 10*

| Analyte Masses = Film Length x Concentration | | | |
|---|---|---|---|
| N ppt | $N_1$ ppt | $N_2$ ppt | $N_3$ ppt |
| A ∞ x1 | 500x100 | 5x10,000 | 1x 50,000 |
| B ∞ x1 | 1,000x100 | 10x10,000 | 1x 100,000 |
| C ∞ x1 | 5,000x100 | 50x10,000 | 1x 500,000 |
| D ∞ x1 | 10,000x100 | 100x10,000 | 1x 520,000+loss |
| E ∞ x1 | 100,000x100 | 1,000x10,000 | 10x 1,000,000 ($10^7$) |

Pres. Drop at 100 cm/s, 100x100 µm

| No. of Elem. N1 - | Length L cm | Pres. Drop $\Delta p$ psi | Peak P. Q watts |
|---|---|---|---|
| 50 | 0.5 | 2.629 | 20.5 |
| 505 | 0.1 | 5.311 | 41.3 |
| 1010 | 0.1 | 10.621 | 82.6 |

*Figure 20*

Table: Design of μGc-μGC System on the Basis of a PHASED Structure

| | v in cm/s | ID in cm | L in cm | s in μm | l in mm | V in cm³/min | Δp in psi |
|---|---|---|---|---|---|---|---|
| μGC-1 | 50 | 0.014 | 25 | 1 | 5 | 0.588 | .671 |
| μGC-2 | 250 | 0.007 | 10 | 0.15 | 2.5 | 0.588 | 5.365 |

| | Half-Width | | k=6 | k=0.2 | k=2 | k=2 | k=0.2 |
|---|---|---|---|---|---|---|---|
| | v cm/s | t₀ ms | Δt ms | tR sec | v(optimal) cm/s | v(optimal) cm/s | R | ΔR(v-vo) % |
| μGC-1 | 50 | 500 | 20 | 3.00 | 68.8 | 56 | 8.76 | 2.5 |
| μGC-2 | 250 | 40 | 2 | 0.24 | 149.2 | 118 | 8.00 | 6.2 |

*Figure 24*

PHASED MICRO ANALYZER VIII

This application is a divisional application of patent application Ser. No. 10/829,763, filed Apr. 21, 2004 now U.S. Pat. No. 7,530,257, entitled, "PHASED MICRO ANALYZER VIII", which is a continuation-in-part of U.S. patent application Ser. No. 10/672,483, filed Sep. 26, 2003, and entitled "PHASED MICRO ANALYZER V, VI", now U.S. Pat. No. 7,367,216, issued May 6, 2008 which is incorporated herein by reference, which claims the benefit of U.S. Provisional Patent Application No. 60/500,821, filed Sep. 4, 2003, the benefit of U.S. Provisional Patent Application No. 60/440,108, filed Jan. 15, 2003, and the benefit of U.S. Provisional Patent Application No. 60/414,211, filed Sep. 27, 2002.

The present application is a Continuation-in-part of pending patent application Ser. No. 10/749,863, filed Dec. 31, 2003, which claims priority under 35 U.S.C. §119(e)(1) from Provisional Patent Application No. 60/440,108, filed Jan. 15, 2003.

The present application is a Continuation-in-part of pending patent application Ser. No. 10/749,863, filed Dec. 31, 2003, which claims priority under 35 U.S.C. §119(e)(1) from Provisional Patent Application No. 60/500,821, filed Sep. 4, 2003.

The present application is a Continuation-in-part of pending patent application Ser. No. 10/749,863, filed Dec. 31, 2003, which claims priority as a Continuation-in-part of patent application Ser. No. 10/672,483, filed Sep. 26, 2003, which claims the benefit of Provisional Application No. 60/414,211, filed Sep. 27, 2002.

The present application is a Continuation-in-part of pending patent application Ser. No. 10/749,863, filed Dec. 31, 2003, which claims priority as a Continuation-in-part to patent application Ser. No. 10/671,930, filed Sep. 26, 2003.

The present application is Continuation-in-part of patent application Ser. No. 10/671,930 filed Sep. 26, 2003, which claims priority under 35 U.S.C. 119(e)(1) from Provisional Patent Application No. 60/500,821, filed Sep. 4, 2003, from Provisional Patent Application No. 60/440,108, filed Jan. 15, 2003, and from Provisional Patent Application No. 60/414,211, filed Sep. 27, 2002.

BACKGROUND

The present invention pertains to detection of fluids. Particularly, the invention pertains to a phased heater array structure, and more particularly to application of the structure as a sensor for the identification and quantification of fluid components. It may be referred to as a "PHASED" sensor. The term "fluid" may be used as a generic term that includes gases and liquids as species. For instance, air, gas, water and oil are fluids.

Aspects of structures and processes related to fluid analyzers may be disclosed in U.S. Pat. No. 6,393,894 B1, issued May 28, 2002, to Ulrich Bonne et al., and entitled "Gas Sensor with Phased Heaters for Increased Sensitivity," which is incorporated herein by reference; U.S. Pat. No. 6,308,553 B1, issued Oct. 30, 2001, to Ulrich Bonne et al., and entitled "Self-Normalizing Flow Sensor and Method for the Same," which is incorporated herein by reference; and U.S. Pat. No. 4,944,035, issued Jul. 24, 1990, to Roger L. Aagard et al., and entitled "Measurement of Thermal Conductivity and Specific Heat," which is incorporated herein by reference.

Presently available gas composition analyzers may be selective and sensitive but lack the capability to identify the component(s) of a sample gas mixture with unknown components, besides being generally bulky and costly. The state-of-the-art combination analyzers GC-GC and GC-MS (gas chromatograph-mass spectrometer) approach the desirable combination of selectivity, sensitivity and smartness, yet are bulky, costly, slow and unsuitable for battery-powered applications. In GC-AED (gas chromatograph-atomic emission detector), the AED alone uses more than 100 watts, uses water cooling, has greater than 10 MHz microwave discharges and are costly.

The phased heater array sensor initially consisted of separate chips for the concentrator, the separator, as well as for an off-chip flow sensor. These may be integrated onto one chip and provide improvements in the structural integrity and temperature control while reducing power consumption. The next phased heater array sensor involved an addition of integratable, micro-discharge devices for detection, identification and quantification of analyte. However, short of the full integration of the FET switches and shift register(s) onto the chip, there still was a need to wire-bond, route, connect and route many wires from a daughter-board to mother-board with its micro-processor-controlled FET switches, which caused bulk and labor cost. In addition, the phased heater array sensor analyzers and conventional GCs seem to lack flexibility to change pre-concentration and separation capabilities on-line.

Detection, identification and analysis of very small amounts of fluids in a more inexpensive, efficient, low power, portable and inexpensive manner, than in the related art, are desired.

SUMMARY

The present invention is a miniaturized and highly accurate fluid micro analyzer utilizing a chromatograph configuration. It is a very energy-efficient analyzer that may be battery-powered and used as a portable instrument.

BRIEF DESCRIPTION OF THE DRAWING

FIG. 10 is a table showing detection limits and selectivities for various elements;

FIG. 20 is a table showing the pressure change relative to the number of elements of a MEMs channel;

FIG. 24 is a table of design and performance data of a double gas chromatograph system having a phased heater structure;

DESCRIPTION

Figure 1:
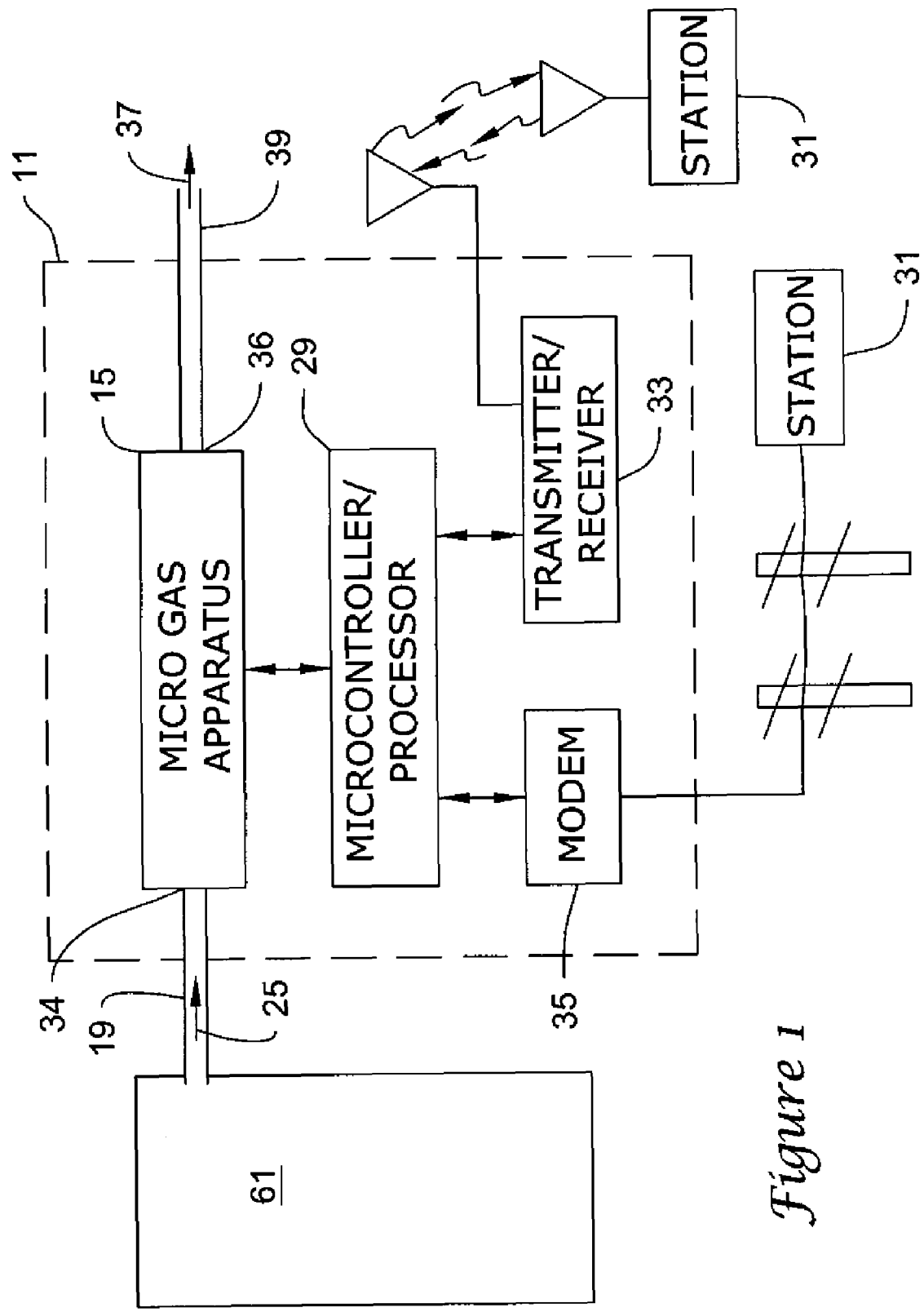
FIG. 1 is a diagram of a sensor system.

The device may be a sensor system/micro analyzer consisting of an array of selective, sensitive, fast and low-power phased heater elements in conjunction with an array of compact, fast, low-power, ambient pressure, minimal pumping mass spectral analysis devices to achieve fluid component presence, identification and quantification. The device may be very small, energy-efficient and portable including its own power source.

The micro fluid analyzer may have one or more concentrators and two or more separators. The analyzer may have one, two or more pumps. The analyzer may have a pre-concentrator having a number of channels. There may be numerous detectors positioned along the flow path of the analyzer. Also, one or more orifices and micro valves may be positioned in the flow path. The concentrator may have an array of phased heater elements that provide a heat pulse to generate a desorbed-analyte concentration pulse that moves along the fluid path to provide an increasing concentration of analytes. The analyzer may be configured as a multiple fluid or gas chromatograph.

Additionally, flexibility, low cost and compactness features are incorporated via FET switches, shift registers and control logic onto the same or a separate chip connected to the phased heater array sensor chip via wire-bonds or solder-bumps on the daughter-PCB (printed circuit board connected to the mother-PCB via only about ten leads) and providing the user flexibility to be able select the fraction of total heatable elements for pre-concentration and separation; and selection of analysis logic.

Multi-fluid detection and analysis may be automated via affordable, in-situ, ultra-sensitive, low-power, low-maintenance and compact micro detectors and analyzers, which can wirelessly or by another medium (e.g., wire or optical fiber) send their detection and/or analysis results to a central or other manned station. A micro fluid analyzer may incorporate a phased heater array, concentrator, separator and diverse approaches. The micro fluid analyzer may be a low-cost approach to sense ozone with a several parts-per-billion (ppb) maximum emission objective. The analyzer may be capable of detecting a mixture of trace compounds in a host or base sample gas or of trace compounds in a host liquid.

The fluid analyzer may include a connection to an associated microcontroller or processor. An application of the sensor may include the detection and analyses of air pollutants in aircraft space such as aldehydes, butyric acid, toluene, hexane, and the like, besides the conventional $CO_2$, $H_2O$ and CO. Other sensing may include conditioned indoor space for levels of gases such as $CO_2$, $H_2O$, aldehydes, hydrocarbons and alcohols, and sensing outdoor space and process streams of industries such as in chemical, refining, product purity, food, paper, metal, glass, medical and pharmaceutical industries. Also, sensing may have a significant place in environmental assurance and protection. Sensing may provide defensive security in and outside of facilities by early detection of chemicals before their concentrations increase and become harmful.

A vast portion of the sensor may be integrated on a chip with conventional semiconductor processes or micro electromechanical system (MEMS) techniques. This kind of fabrication results in small, low-power consumption, and in situ placement of the micro analyzer. The flow rate of the air or gas sample through the monitor may also be very small. Further, a carrier gas for the samples is not necessarily required and thus this lack of carrier gas may reduce the dilution of the samples being tested, besides eliminating the associated maintenance and bulk of pressurized gas-tank handling. This approach permits the sensor to provide quick analyses and prompt results, may be at least an order of magnitude faster than some related art devices. It avoids the delay and costs of labor-intensive laboratory analyses. The sensor is intelligent in that it may have an integrated microcontroller for analysis and determination of gases detected, and may maintain accuracy, successfully operate and communicate information in and from unattended remote locations. The sensor may communicate detector information, analyses and results via utility lines, or optical or wireless media, with the capability of full duplex communication to a host system over a significant distance with "plug-and-play" adaptation and simplicity. The sensor may be net-workable. It may be inter-connectable with other gas sample conditioning devices (e.g., particle filters, valves, flow and pressure sensors), local maintenance control points, and can provide monitoring via the internet. The sensor is robust. It can maintain accuracy in high electromagnetic interference (EMI) environments having very strong electrical and magnetic fields. The sensor has high sensitivity. The sensor offers sub-ppm or sub-ppb level detection which is 100 to more than 10,000 times better than related art technology, such as conventional gas chromatographs which may offer a sensitivity in a 1 to 10 ppm range. The sensor is, among other things, a lower-power, faster, and more compact, more sensitive and affordable version of a gas chromatograph. It may have structural integrity and have very low or no risk of leakage in the application of detecting and analyzing pressurized fluid samples over a very large differential pressure range.

In the sensor, a small pump, such as a Honeywell MesoPump™, may draw a sample into the system, while only a portion of it might flow through the phased heater sensor at a rate controlled by the valve (which may be a Honeywell MesoValve™ or Hoerbiger PiezoValve™). This approach may enable fast sample acquisition despite long sampling lines, and yet provide a regulated, approximately 0.1 to 3 $cm^3$/min flow for the detector. The pump of the sensor may be arranged to draw sample gas through a filter in such a way as to provide both fast sample acquisition and regulated flow through the phased heater sensor.

As a pump draws sample gas through the sensor, the gas may expand and thus increase its volume and linear velocity. The control circuit may be designed to compensate for this change in velocity to keep the heater "wave" in sync with the varying gas velocity in the sensor. To compensate for the change in sample gas volume as it is forced through the heater channels, its electronics may need to adjust either the flow control and/or the heater "wave" speed to keep the internal gas flow velocity in sync with the electric-driven heater "wave".

During a gas survey operation, the sensor's ability (like any other slower gas chromatographs) may sense multiple trace constituents of air such as about 330 to 700 ppm of $CO_2$, about 1 to 2 ppm of $CH_4$ and about 0.5 to 2.5 percent of $H_2O$. This may enable on-line calibration of the output elution times as well as checking of the presence of additional peaks such as ethane, possibly indicating a natural gas, propane or other gas pipeline leak. The ratio of sample gas constituent peak heights thus may reveal clues about the source of the trace gases, which could include car exhaust or gasoline vapors.

The sensor may have the sensitivity, speed, portability and low power that make the sensor especially well suited for safety-mandated periodic leak surveys of natural gas or propane gas along transmission or distribution pipeline systems and other gas in chemical process plants.

The sensor may in its leak sensing application use some or all sample gas constituents (and their peak ratios) as calibration markers (elution time identifies the nature of the gas constituents) and/or as leak source identifiers. If the presence alone of a certain peak such as methane (which is present in mountain air at about one to two ppm) may not be enough information to indicate that the source of that constituent is from swamp gas, a natural or pipeline gas or another fluid.

The sensor may be used as a portable device or installed at a fixed location. In contrast to comparable related art sensors, it may be more compact than a portable flame ionization detector without requiring the bulkiness of hydrogen tanks, it may be faster and more sensitive than hot-filament or metal oxide combustible gas sensors, and much faster, more compact and more power-thrifty than conventional and/or portable gas chromatographs.

Detection and analysis by sensor 15 of FIG. 1 may include detection, identification and quantification of fluid components. That may include a determination of the concentration of or parts-per-million of the fluid detected. Sensor 15 may be used to detect fluids in the environment. Also, sensor 15 may detect miniscule amounts of pollutants in ambient environment of a conditioned or tested space. Sensor 15 may indicate the health and the level of toxins-to-people in ambient air or exhaled air.

FIG. 1 reveals an illustrative diagram of a low-power sensor system 11. A sample fluid 25 from a process stream, an ambient space or volume 61 may enter a conduit or tube 19 which is connected to an input 34 of a sensor or micro gas apparatus 15. Fluid 25 may be processed by sensor 15. Processed fluid 37 may exit output 36 of sensor 15 and be exhausted to volume 61 or another volume, wherever designated, via a conduit or tube 39.

Sensor 15 results may be sent to microcontroller/processor 29 for analysis, and nearly immediate conclusions and results. This information may be sent on to observer stations 31 for review and further analysis, evaluation, and decisions about the results found. Data and control information may be sent from stations 31 to microcontroller/processor 29. Data and information may be sent and received via the wireless medium by a transmitter/receiver 33 at sensor 11 and at stations 31. Or the data and information may be sent and received via wire or optical lines of communication by a modem 35 at monitor 11 and station 31. The data and information may be sent to a SCADA (supervisory control and data acquisition) system. These systems may be used in industry (processing, manufacturing, service, health and so forth) to detect certain gases and provide information relating to the detection to remote recipients.

Microcontroller or processor 29 may send various signals to analyzer 15 for control, adjustment, calibration or other purposes. Also, microcontroller/processor 29 may be programmed to provide a prognosis of the environment based on detection results. The analysis calculations, results or other information may be sent to modem 35 for conversion into signals to be sent to a station 31 via lines, fiber or other like media. Also, such output to modem 35 may be instead or simultaneously sent to transmitter 33 for wireless transmission to a station 31, together with information on the actual location of the detection obtained, e.g., via GPS, especially if it is being used as a portable device. Also, stations 31 may send various signals to modem 35 and receiver 33, which may be passed on to microcontroller or processor 29 for control, adjustment, calibration or other purposes.

In FIG. 1, space 61 may be open or closed. Sensor system 11 may have a hook-up that is useable in a closed space 61 such as an aircraft-cabin, machinery room, factory, or some place in another environment. Or it may be useable in an open space 61 of the earth's environment. The end of input tube or pipe 19 may be in open space 61 and exhaust of exit tube 37 may be placed at a distance somewhat removed from a closed space 61. System 11 for space 61 may itself be within space 61 except that tube 39 may exit into space 61, especially downstream in case space 61 is a process stream.

Figure 2:
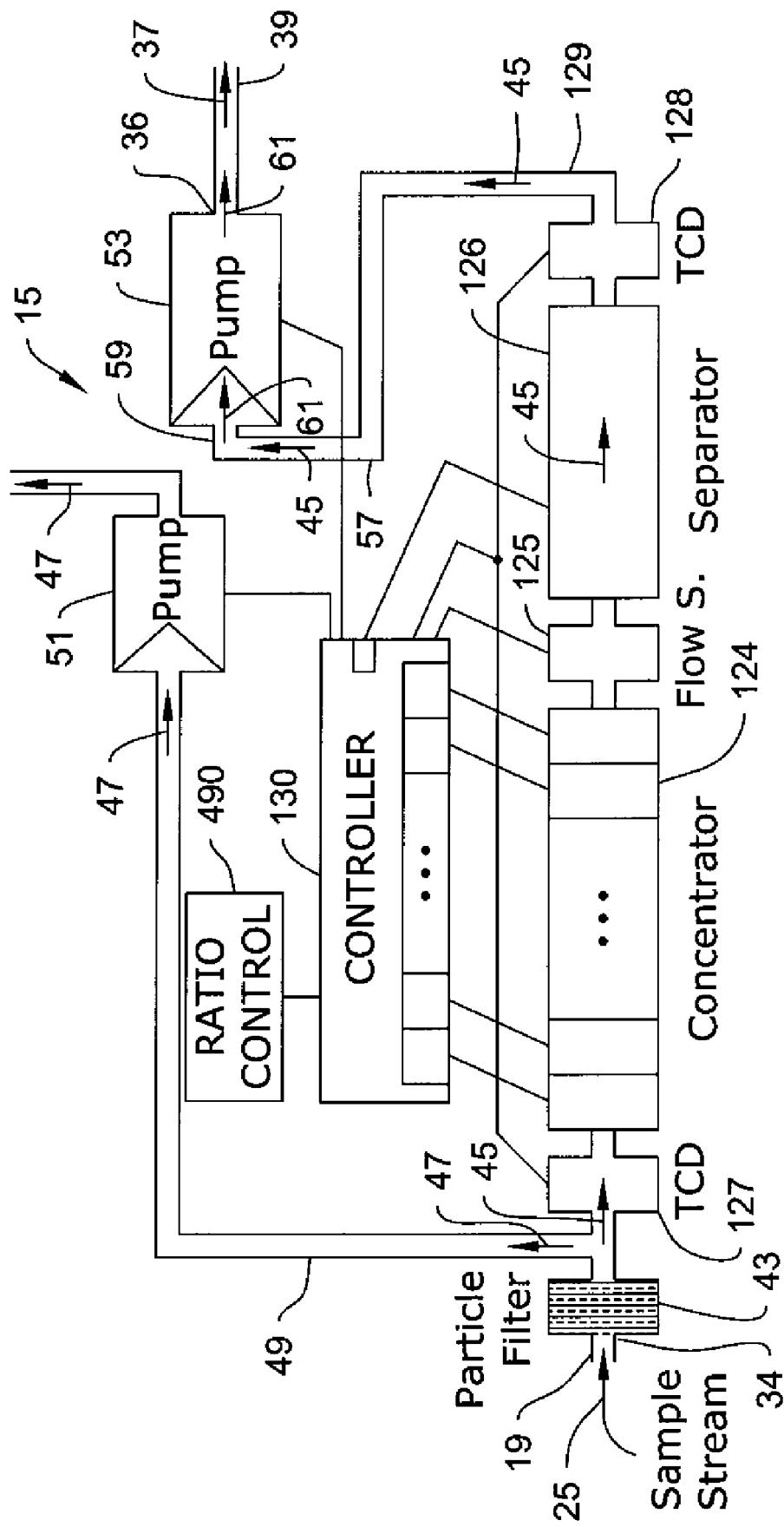
FIG. 2 shows details of a micro gas apparatus.

FIG. 2 reveals certain details of micro gas apparatus 15. Further details and variants of it are described below in conjunction with subsequent figures. Sample stream 25 may enter input port 34 from pipe or tube 19. There may be a particle filter 43 for removing dirt and other particles from the stream of fluid 25 that is to enter apparatus 15. This removal is for the protection of the apparatus and the filtering should not reduce the apparatus' ability to accurately analyze the composition of fluid 25. Dirty fluid (with suspended solid or liquid non-volatile particles) might impair proper sensor function. A portion 45 of fluid 25 may flow through the first leg of a differential thermal-conductivity detector (TCD), or chemi-sensor (CRD), or photo-ionization sensor/detector (PID), or other device) 127 which may measure photo-ionization current, and a portion 47 of fluid 25 flows through tube 49 to a pump 51. By placing a "T" tube immediately adjacent to the inlet 45, sampling with minimal time delay may be achieved because of the relatively higher flow 47 to help shorten the filter purge time. Pump 51 may cause fluid 47 to flow from the output of particle filter 43 through tube 49 and exit from pump 51. Pump 53 may effect a flow of fluid 45 through the sensor via tube 57. Pump 51 may now provide suction capacity of 10-300 $cm^3$/min at less than 1 psi pressure drop ($\Delta p$) and low-flow-capacity pump 53 may provide 0.1-3 cm3/min at up to a $\Delta p$ of 10 psi). There may be additional or fewer pumps, and various tube or plumbing arrangements or configurations for system 15 in FIG. 2. Data from detectors 127 and 128 may be sent to control 130, which in turn may relay data to microcontroller and/or processor 29 for processing. Resultant information may be sent to station 31.

Pumps 51 and 53 may be very thrifty and efficient configurations implemented for pulling in a sample of the fluid being checked for detection of possible gas from somewhere. Low-power electronics having a sleep mode when not in use may be utilized. The use of this particularly thrifty but adequately functional pump 51 and 53, which may run only about or less than 1-10 seconds before the start of a concentrator and/or measurement cycle of analyzer system 11, and the use of low-power electronics for control 130 and/or microcontroller/processor 29 (which may use a sleep mode when not in use) might result in about a two times reduction in usage of such power.

Figure 3:
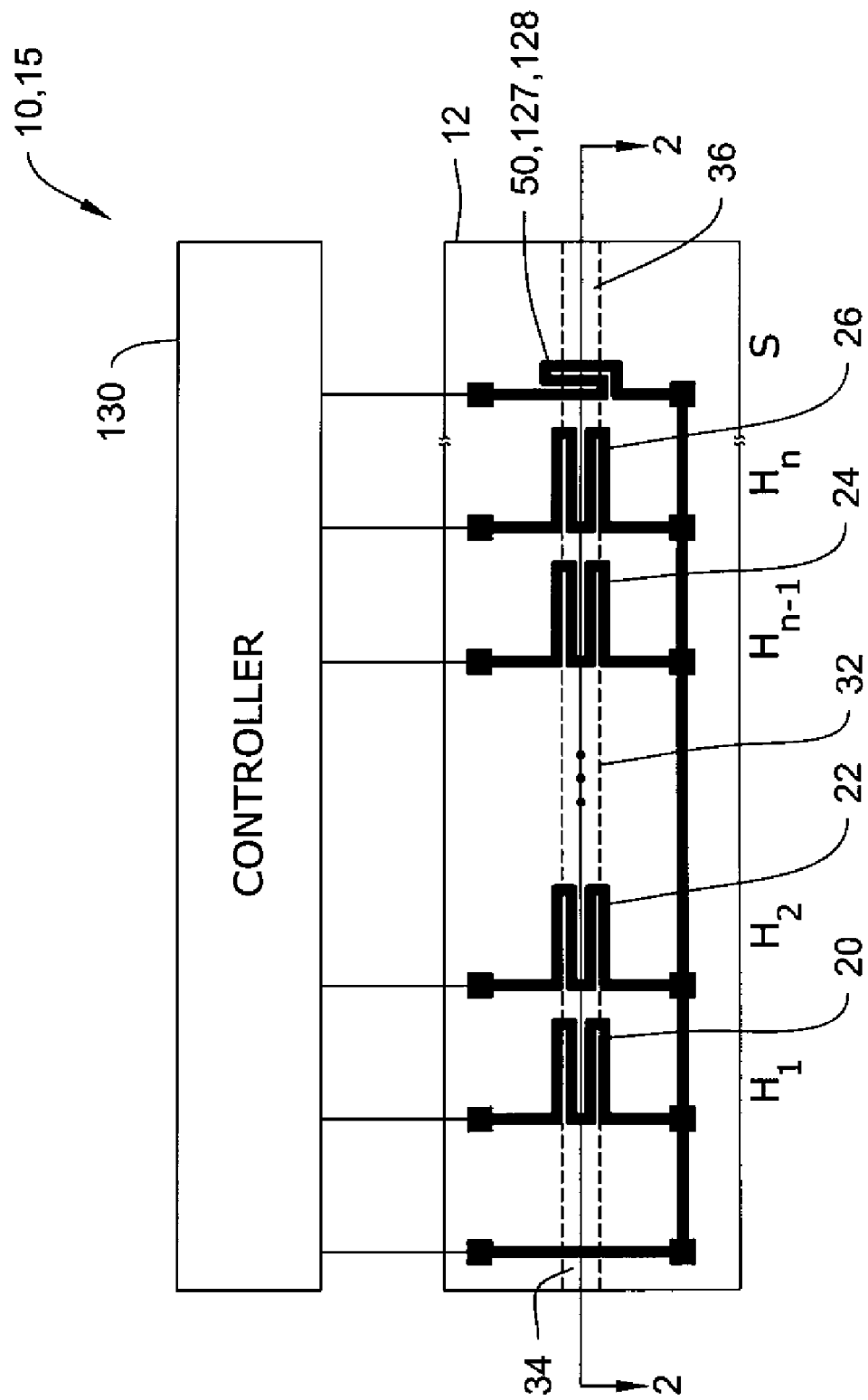
FIG. 3 is a layout of an illustrative phased heater mechanism.
Figure 4:
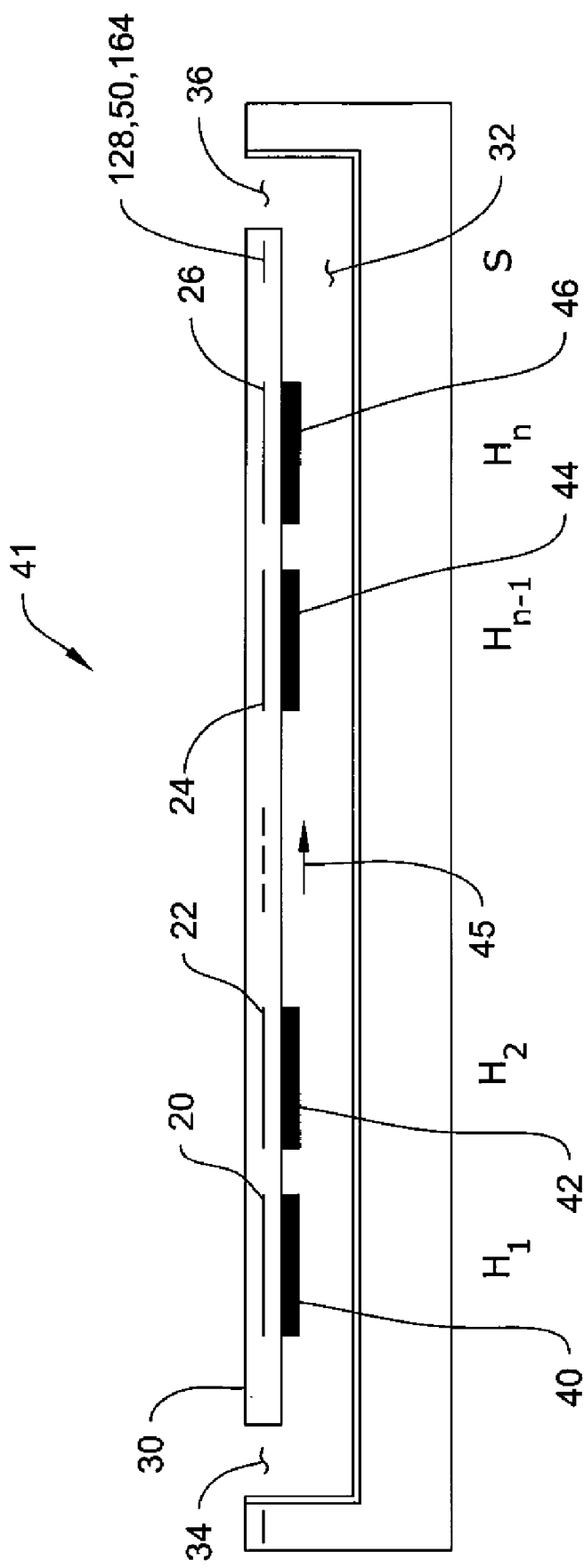
FIG. 4 is a length-wise sectional view of a heater elements on a straightened channel.
Figure 5:
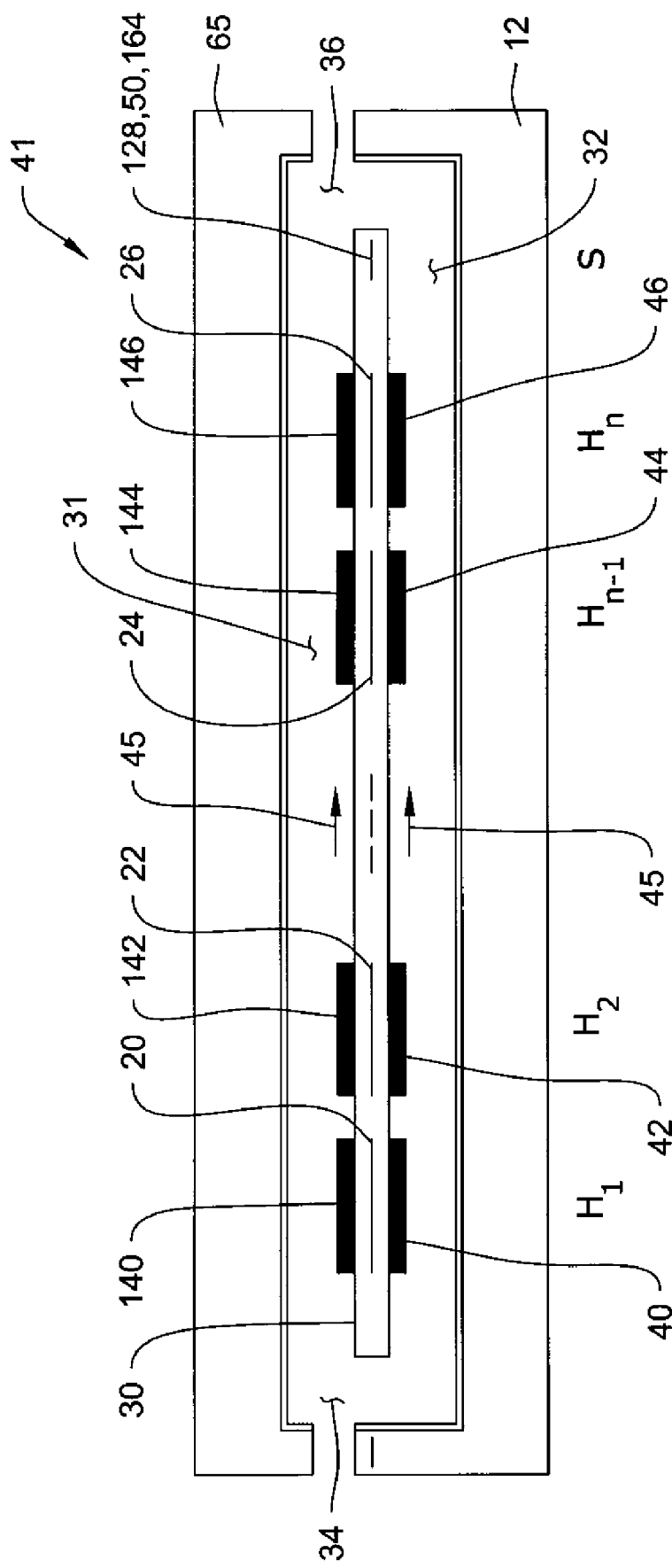
FIG. 5 is a length-wise sectional view of a twin-film heater elements on a straightened channel.

FIG. 3 is a schematic diagram of part of the sensor apparatus 10, 15, representing a portion of concentrator 124 or separator 126 in FIG. 2. The sensor apparatus may include a substrate 12 and a controller 130. Controller 130 may or may not be incorporated into substrate 12. Substrate 12 may have a number of thin film heater elements 20, 22, 24, and 26 positioned thereon. While only four heater elements are shown, any number of heater elements may be provided, for instance, between two and one thousand, but typically in the 20-100 range. Heater elements 20, 22, 24, and 26 may be fabricated of any suitable electrical conductor, stable metal, or alloy film, such as a nickel-iron alloy sometimes referred to as permalloy having a composition of eighty percent nickel and twenty percent iron; platinum, platinum silicide and polysilicon. Heater elements 20, 22, 24, and 26 may be provided on a thin, low-thermal mass, low-in-plane thermal conduction, support member 30, as shown in FIGS. 4 and 5. Support member or membrane 30 may be made from $Si_3N_4$ or other appropriate or like material. The heater elements may be made from Pt or other appropriate or like material.

Substrate 12 may have a well-defined single-channel phased heater mechanism 41 having a channel 32 for receiving the sample fluid stream 45, as shown in FIG. 4. FIG. 5 reveals a double-channel phased heater design 41 having channels 31 and 32. Substrate 12 and portion or wafer 65 may have defined channels 31 and 32 for receiving a streaming sample fluid 45. The channels may be fabricated by selectively etching silicon channel wafer substrate 12 beneath support member 30 and wafer or portion 65 above the support member. The channels may include an entry port 34 and an exhaust port 36.

The sensor apparatus may also include a number of interactive elements inside channels 31 and 32 so that they are exposed to the streaming sample fluid 45. Each of the interactive elements may be positioned adjacent, i.e., for closest possible contact, to a corresponding heater element. For example, in FIG. 4, interactive elements 40, 42, 44, and 46 may be provided on the lower surface of support member 30 in channel 32, and be adjacent to heater elements 20, 22, 24, and 26, respectively. In FIG. 5, additional interactive elements 140, 142, 144, and 146 may be provided on the upper surface of support member 30 in second channel 31, and also adjacent to heater elements 20, 22, 24, and 26, respectively. There may be other channels with additional interactive film elements which are not shown in the present illustrative example. The interactive elements may be formed from any number of films commonly used in liquid or gas chromatography, such as silica gel, polymethylsiloxane, polydimethylsiloxane, polyethyleneglycol, porous silica, Nanoglass™, active carbon, and other polymeric substances. Furthermore, the above interactive substances may be modified by suitable dopants to achieve varying degrees of polarity and/or hydrophobicity, to achieve optimal adsorption and/or separation of targeted analytes.

Figure 6A:
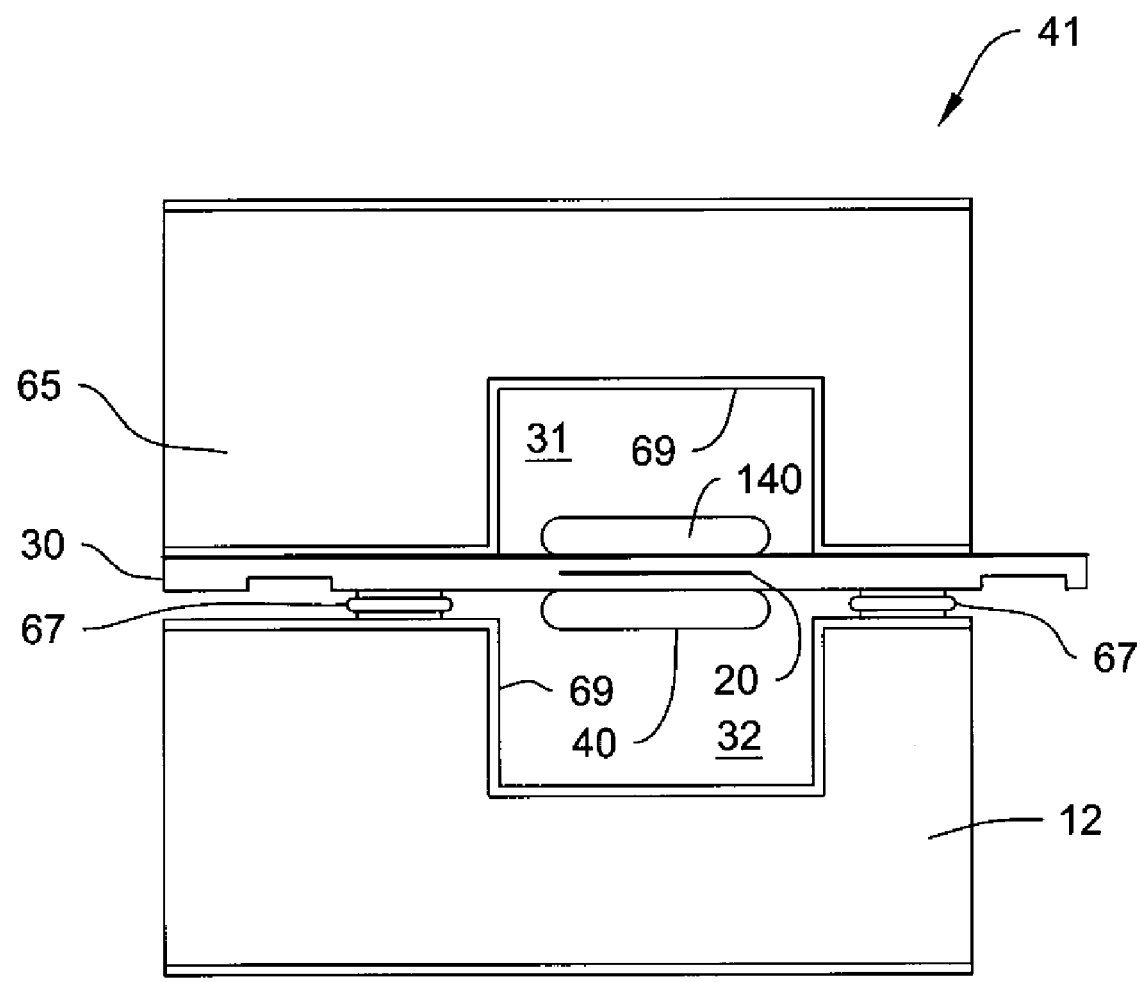
FIGS. 6a, 6b and 6c show cross-section end views of the twin-film heater element and single film element.
Figure 6C:
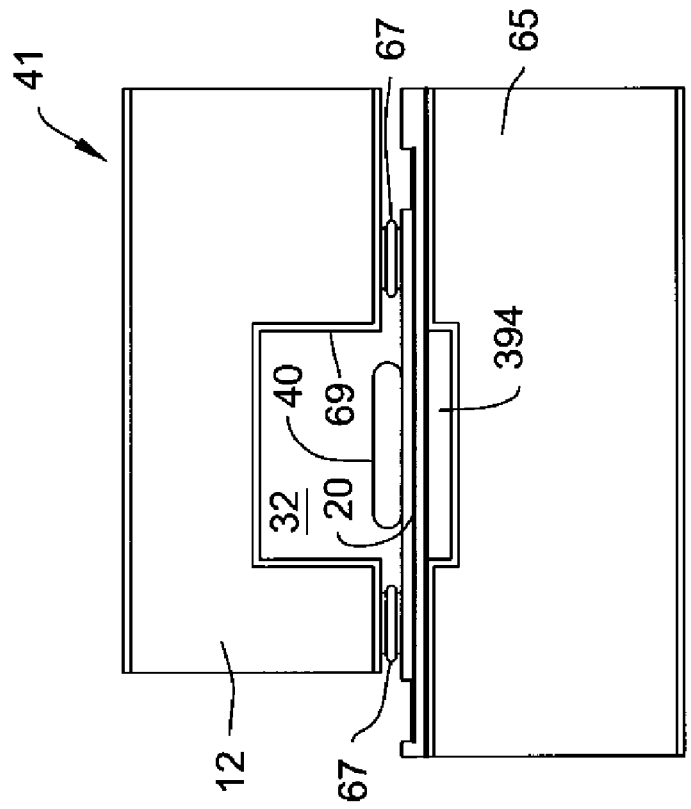
Figure 6B:
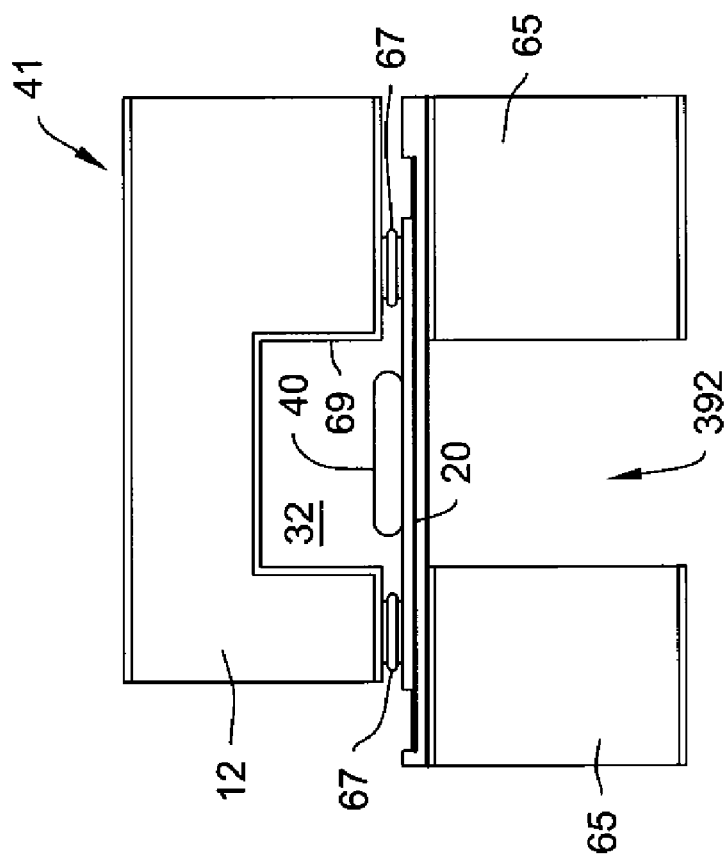

FIG. 6a shows a cross-section end view of two-channel phased heater mechanism 41. The top and bottom perspectives of portions in FIGS. 6a, 6b and 6c may not necessarily appear to be the same. An end view of a single channel phased heater mechanism 41 may incorporate the support member 30 and substrate 12 and the items between them, in FIGS. 6b and 6c. FIG. 6b shows a version of the phased heater mechanism 41 having an exposed 1 micron membrane. Shown in FIG. 6b is open space 392. FIG. 6c shows a ruggedized, low power version having a small closed space 394. Support member 30 may be attached to top structure 65. Anchors 67 may hold support member 30 in place relative to channel 31. Fewer anchor 67 points minimize heat conduction losses from support 30 to other portions of structure 41. There may be a heater membrane that has a small number anchor points for little heat conduction from the heater elements. In contrast to a normal anchoring scheme, the present example may have a reduction of anchor points to result in the saving about 1.5 times of the remaining heater element input power.

The heater elements of a phased heater array may be coated with an adsorber material on both surfaces, i.e., top and bottom sides, for less power dissipation and more efficient heating of the incoming detected gas. The heater elements may have small widths for reduced power dissipation.

Interactive film elements may be formed by passing a stream of material carrying the desired sorbent material through channel 32 of single-channel heating mechanism 41. This may provide an interactive layer throughout the channel. If separate interactive elements 40, 42, 44, 46 are desired, the coating may be spin-coated onto substrate 30 attached to the bottom wafer 12, before attaching the top wafer 65 in FIG. 6a, and then selectively "developed" by either using standard photoresist masking and patterning methods or by providing a temperature change to the coating, via heater elements 20, 22, 24 and 26.

The surfaces of inside channel of the heater array, except those surfaces intentionally by design coated with an adsorber material, may be coated with a non-adsorbing, thermal insulating layer. The thickness of the adsorber coating or film may be reduced thereby decreasing the time needed for adsorption and desorption. As in FIG. 6a, coating 69 of a non-adsorbing, thermal insulating material may be applied to the inside walls of channel 31 in the single-channel heater 41, and the wall of channels 31 and 32 in the dual-channel heater mechanism 41, except where there is adsorber coated surfaces, by design, such as the interactive elements. Coating 69 may reduce the needed heater element power by about 1.5 times. The material should have thermal conduction that is substantially less than the material used in the channel walls. The latter may be silicon. Alternative materials for coating 69 may include $SiO_2$ or other metal oxides. Coating 69 may reduce power used for the heater elements in support 30. A minimizing or reduction of the size (width, length and thickness) of the heater element membranes as well as the adsorber film, while retaining a reasonable ratio of mobile/stationary phase volume, may result in about a four times power reduction. The minimized or reduced adsorber film thickness may reduce the time needed for adsorption-desorption and save about 1.5 times in energy needed per fluid analysis for a given analyzer structure.

Heater elements 20, 22, 24 and 26 may be GC-film-coated on both the top and bottom sides so that the width and power dissipation of the heater element surface by about two times. The fabrication of these heater elements involves two coating steps, with the second step requiring wafer-to-wafer bonding and coating after protecting the first coat inside the second wafer and dissolving the first wafer.

Another approach achieving the desired ruggedness (i.e. not expose a thin membrane 20, 22, 24, . . . to the exterior environment) but without the need to coat these both top and bottom, is to coat only the top and reduce the bottom channel 32 to a small height, see FIG. 6a, so that the volumetric ratio (air/film) is of a value of less than 500.

The micro gas analyzer may have heater elements 40, 42, . . . , 44, 46 and 140, 142, . . . , 144, 146 fabricated via repeated, sequentially spin-coated (or other deposition means) steps, so that a pre-arranged pattern of concentrator and separator elements are coated with different adsorber materials A, B, C, . . . (known in GC literature as stationary phases), so that not only can the ratio of concentrator/separator elements be chosen, but also which of those coated with A, B, C and so forth may be chosen (and at what desorption temperature) to contribute to the concentration process and electronically be injected into the separator, where again a choice of element temperature ramping rates may be chosen for the A's to be different for the B, C, . . . elements; and furthermore adding versatility to this system in such a way that after separating the gases from the group of "A" elements; another set of gases may be separated from the group of "B" elements, and so forth. The ratio of concentrator to separator heater elements may be set or changed by a ratio control mechanism 490 connected to controller 130.

Controller 130 may be electrically connected to each of the heater elements 20, 22, 24, 26, and detector 50 as shown in FIG. 3. Controller 130 may energize heater elements 20, 22, 24, and 26 in a time phased sequence (see bottom of FIG. 7) such that each of the corresponding interactive elements 40, 42, 44, and 46 become heated and desorb selected constituents into a streaming sample fluid 45 at about the time when an upstream concentration pulse, produced by one or more upstream interactive elements, reaches the interactive element. Any number of interactive elements may be used to achieve the desired concentration of constituent gases in the concentration pulse. The resulting concentration pulse may be provided to detector 50, 128, for detection and analysis. Detector 50, 127, or 128 (FIGS. 2 and 3) may be a thermal-conductivity detector, discharge ionization detector, CRD, PID, MDD, or any other type of detector such as that typically used in gas or fluid chromatography.

Figure 7:
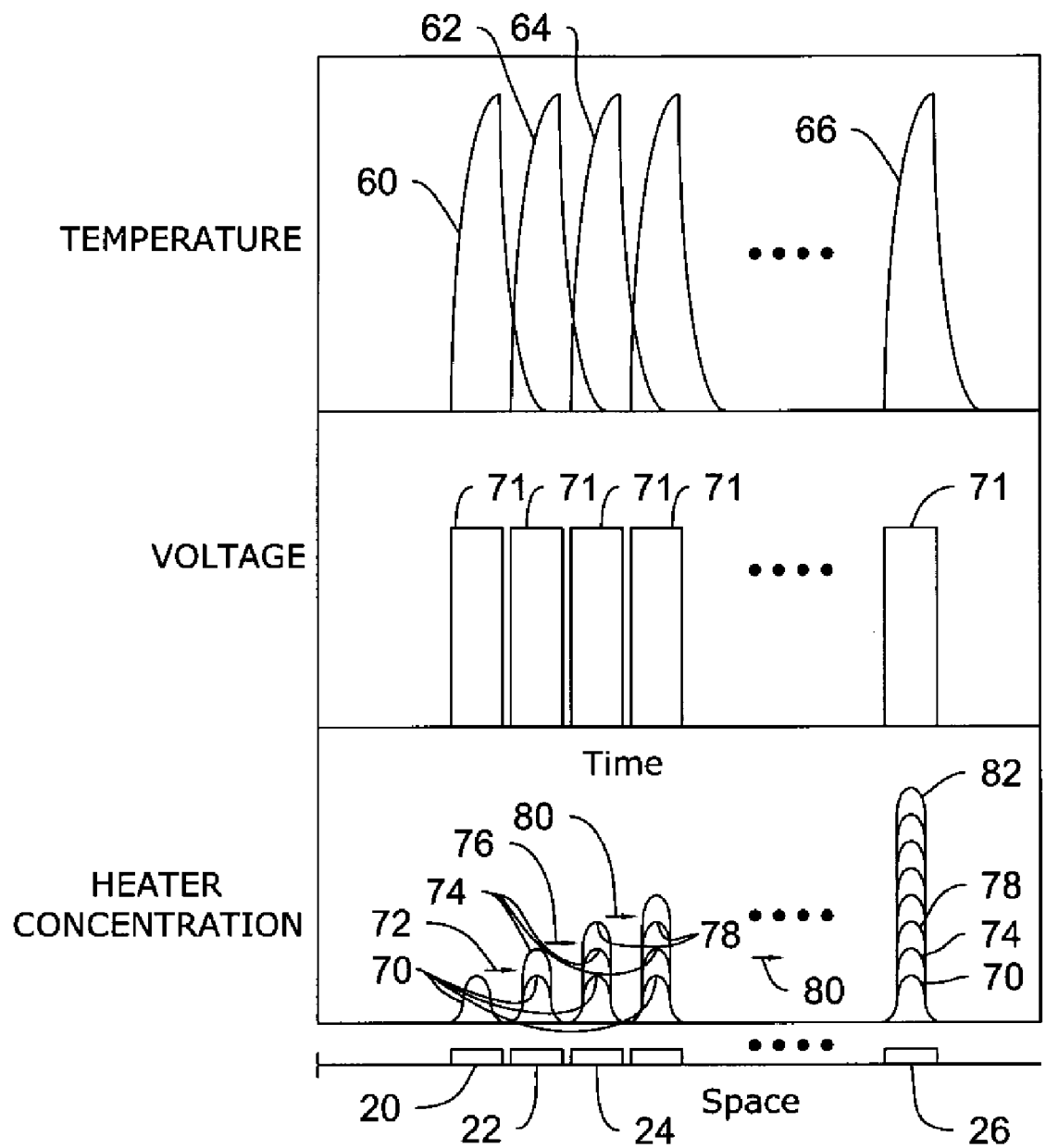
FIG. 7 is a graph illustrating heater temperature profiles, along with corresponding concentration pulses produced at each heater element of the sensor apparatus.

FIG. 7 is a graph showing illustrative relative heater temperatures, along with corresponding concentration pulses produced at each heater element. As indicated above, controller 130 may energize heater elements 20, 22, 24, and 26 in a time phased sequence with voltage signals 71. Illustrative time phased heater relative temperatures for heater elements 20, 22, 24, and 26 are shown by temperature profiles or lines 60, 62, 64, and 66, respectively.

In the example shown, controller 130 (FIG. 3) may first energize first heater element 20 to increase its temperature as shown at line 60 of FIG. 7. Since first heater element 20 is thermally coupled to first interactive element 40 (FIGS. 4 and 5), the first interactive element desorbs selected constituents into the streaming sample fluid 45 to produce a first concentration pulse 70 (FIG. 7) at the detector 128 or 50, if no other heater elements were to be pulsed. The streaming sample fluid 45 carries the first concentration pulse 70 downstream toward second heater element 22, as shown by arrow 72.

Controller 130 may next energize second heater element 22 to increase its temperature as shown at line 62, starting at or before the energy pulse on element 20 has been stopped. Since second heater element 22 is thermally coupled to second interactive element 42, the second interactive element also desorbs selected constituents into streaming sample fluid 45 to produce a second concentration pulse. Controller 130 may energize second heater element 22 such that the second concentration pulse substantially overlaps first concentration pulse 70 to produce a higher concentration pulse 74, as shown in FIG. 7. The streaming sample fluid 45 carries larger concentration pulse 74 downstream toward third heater element 24, as shown by arrow 76.

Controller 130 may then energize third heater element 24 to increase its temperature as shown at line 64 in FIG. 7. Since third heater element 24 is thermally coupled to third interactive element 44, third interactive element 44 may desorb selected constituents into the streaming sample fluid to produce a third concentration pulse. Controller 130 may energize third heater element 24 such that the third concentration pulse substantially overlaps larger concentration pulse 74 provided by first and second heater elements 20 and 22 to produce an even larger concentration pulse 78. The streaming sample fluid 45 carries this larger concentration pulse 78 downstream toward an "Nth" heater element 26, as shown by arrow 80.

Controller 130 may then energize "N-th" heater element 26 to increase its temperature as shown at line 66. Since "N-th" heater element 26 is thermally coupled to an "N-th" interactive element 46, "N-th" interactive element 46 may desorb selected constituents into streaming sample fluid 45 to produce an "N-th" concentration pulse. Controller 130 may energize "N-th" heater element 26 such that the "N-th" concentration pulse substantially overlaps larger concentration pulse 78 provided by the previous N-1 interactive elements. The streaming sample fluid carries "N-th" concentration pulse 82 to either a separator 126 or a detector 50 or 128, as described below.

As indicated above, heater elements 20, 22, 24, and 26 may have a common length. As such, controller 130 can achieve equal temperatures of the heater elements by providing an equal voltage, current, or power pulse to each heater element. The voltage, current, or power pulse may have any desired shape including a triangular shape, a square shape, a bell shape, or any other shape. An approximately square shaped current, power or voltage pulse 71 may be used to achieve temperature profiles 60, 62, 64, and 66 as shown in FIG. 7. The temperature profiles look like that, and note that the desorbed species are generated with a small time delay, relative to the voltage pulses.

Figure 8:
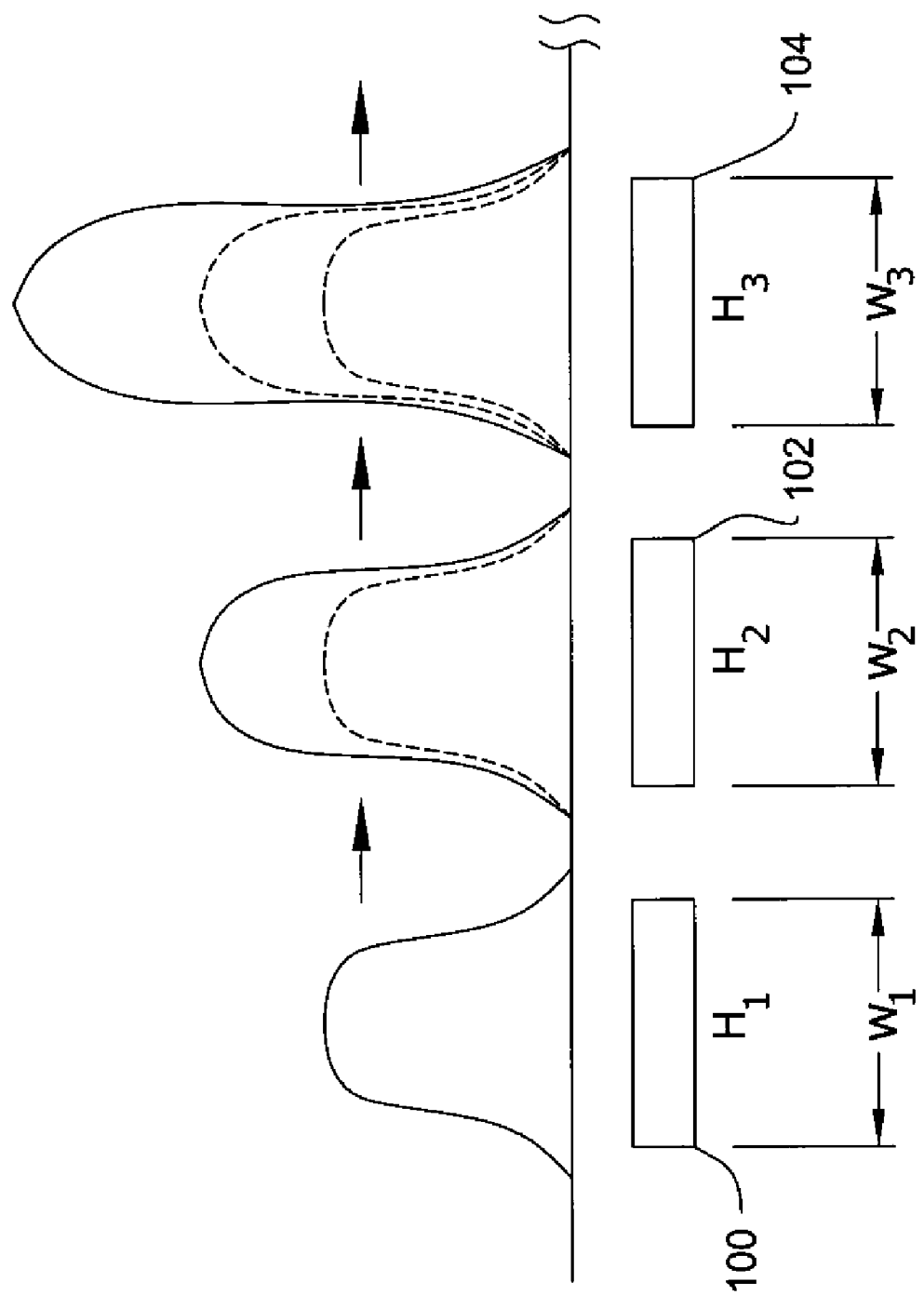
FIG. 8 is a graph showing several heater elements to illustrate a step-wise build-up on an analyte concentration.

FIG. 8 is a graph showing a number of heater elements to illustrate, first, how the concentration increases stepwise as the desorption of subsequent elements is appropriately synchronized with the streaming sample fluid velocity and, second, how the lengths of individual elements are matched to the expected increased rate of mass diffusivity flux as the concentration levels and gradients increase. It should be pointed out here that prior to the elements shown in FIG. 8, the analyte concentration may have been already magnified by a factor, F, by virtue of pulsing an initial element with a length F-times longer than the one shown as element 100 (H1) or, alternatively, by simultaneously pulsing elements 1, 2, . . . , F and collecting all the desorbed analyte with the still cool element 100 (H1), before pulsing it. It is recognized that each of the concentration pulses may tend to decrease in amplitude and increase in length when traveling down channel 32 due to diffusion. To accommodate this increased length, it is contemplated that the length of each successive heater element may be increased along the streaming sample fluid. For example, a second heater element 102 may have a length $W_2$ that is larger than a length $W_1$ of a first heater element 100. Likewise, a third heater element 104 may have a length $W_3$ that is larger than length $W_2$ of second heater element 102. Thus, it is contemplated that the length of each heater element 100, 102, and 104 may be increased, relative to the adjacent upstream heater element, by an amount that corresponds to the expected increased length of the concentration pulse of the upstream heater elements due to diffusion. However, in some cases in which the target analyte concentrations are very small or the adsorbing film capacities are very large, it may be possible and advantageous to significantly decrease the length of subsequent or last heater elements in order to achieve maximum focusing performance of the concentrator function, which is based on minimizing the film volume into which we can adsorb a given quantity of analyte(s) from a given volume of sample gas pumped (pump 51 in FIG. 2) through the concentrator during a given time, and thus increase the analyte(s) concentration by the same ratio of sample volume/film volume (of the last heater element).

To simplify the control of the heater elements, the length of each successive heater element may be kept constant to produce the same overall heater resistance between heater elements, thereby allowing equal voltage, current, or power pulses to be used to produce similar temperature profiles. Alternatively, the heater elements may have different lengths, and the controller may provide different voltage, current, or power pulse amplitudes to the heater element to produce a similar temperature profile.

Figure 9:
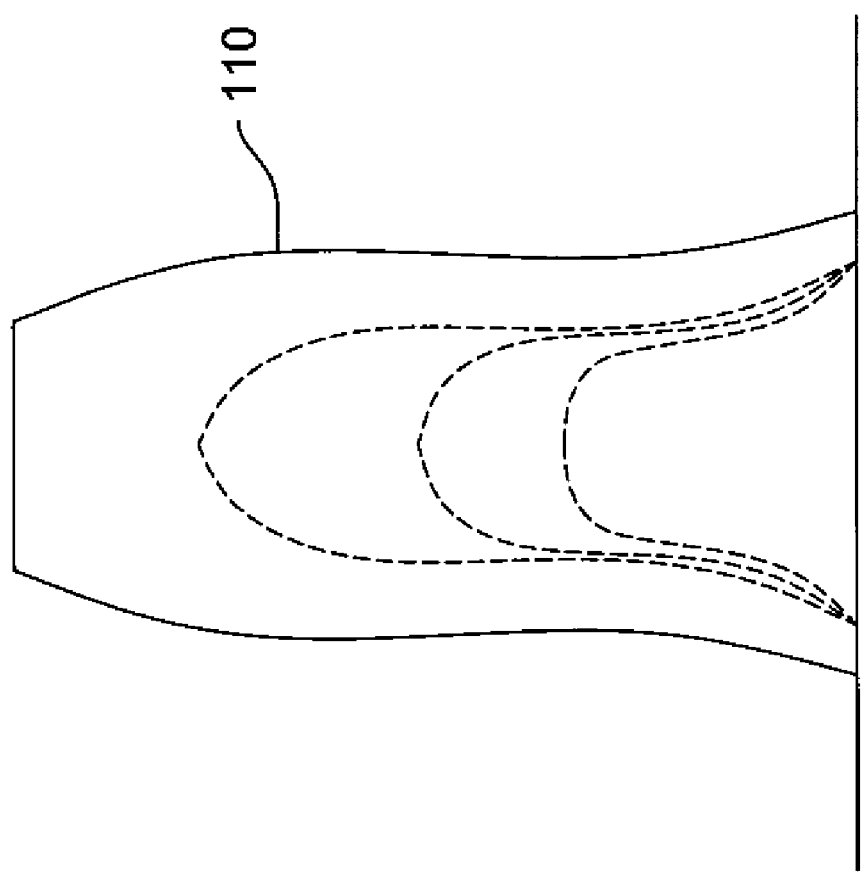
FIG. 9 is a graph showing a concentration pulse that reaches about 100 percent concentration level.

FIG. 9 is a graph showing a concentration pulse 110 that achieves a 100 percent concentration level. It is recognized that even though concentration pulse 110 has achieved a maximum concentration level, such as 100 percent, the concentration of the corresponding constituent can still be determined. To do so, detector 50, 128, 164 may detect the concentration pulse 110, and controller 130 may integrate the output signal of the detector over time to determine the concentration of the corresponding constituent in the original sample of stream 45.

In "GC peak identification", it is desired to associate unequivocally a chemical compound with each gas peak exiting from a gas chromatograph (GC), which is a tool to achieve such separations of individual constituents from each other. There are several approaches for identifying components of a gas. In a GC-MS combination, each GC-peak is analyzed for its mass, while processing the molecular fragments resulting from the required ionization process at the MS inlet. In a GC-GC combination, different separation column materials are used in the first and second GC, in order to add information to the analysis record, which may help with compound identification. In a GC-AED combination, a microwave-powered gas discharge may generate tell-tale optical spectral emission lines (atoms) and bands (molecules) to help identify the gas of the GC-peak in the gas discharge plasma. In the GC-MDD or GC-GC-MDD configurations, the micro discharge device (MDD) may emit spectra of the analyte peaks as they elute from the GC or GC-GC, and reveal molecular and atomic structure and thus identification of the analyte peaks. The MDD may have a detector.

Figure 11:
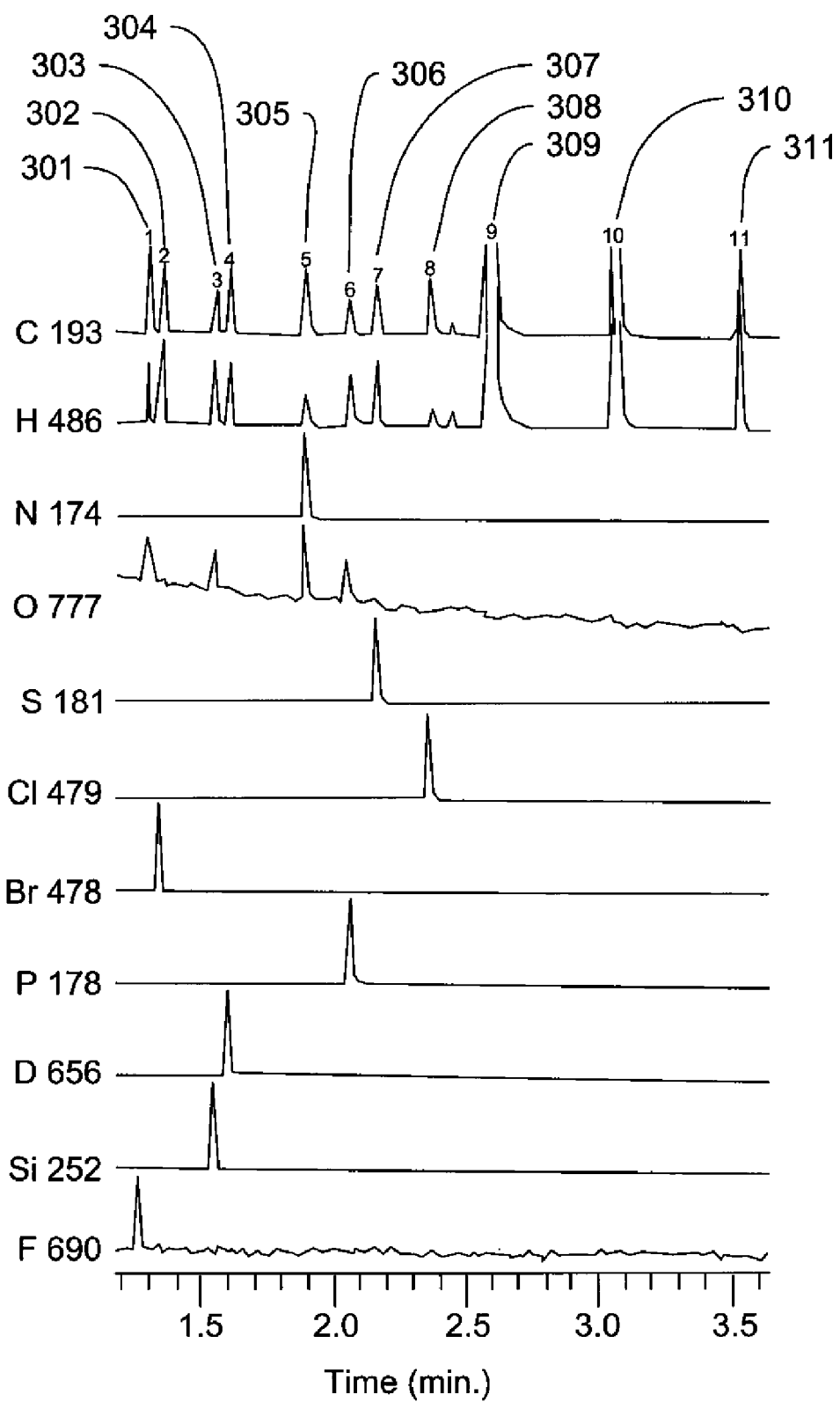
FIG. 11 shows chromatograms of a multielement test mixture.
Figure 12:
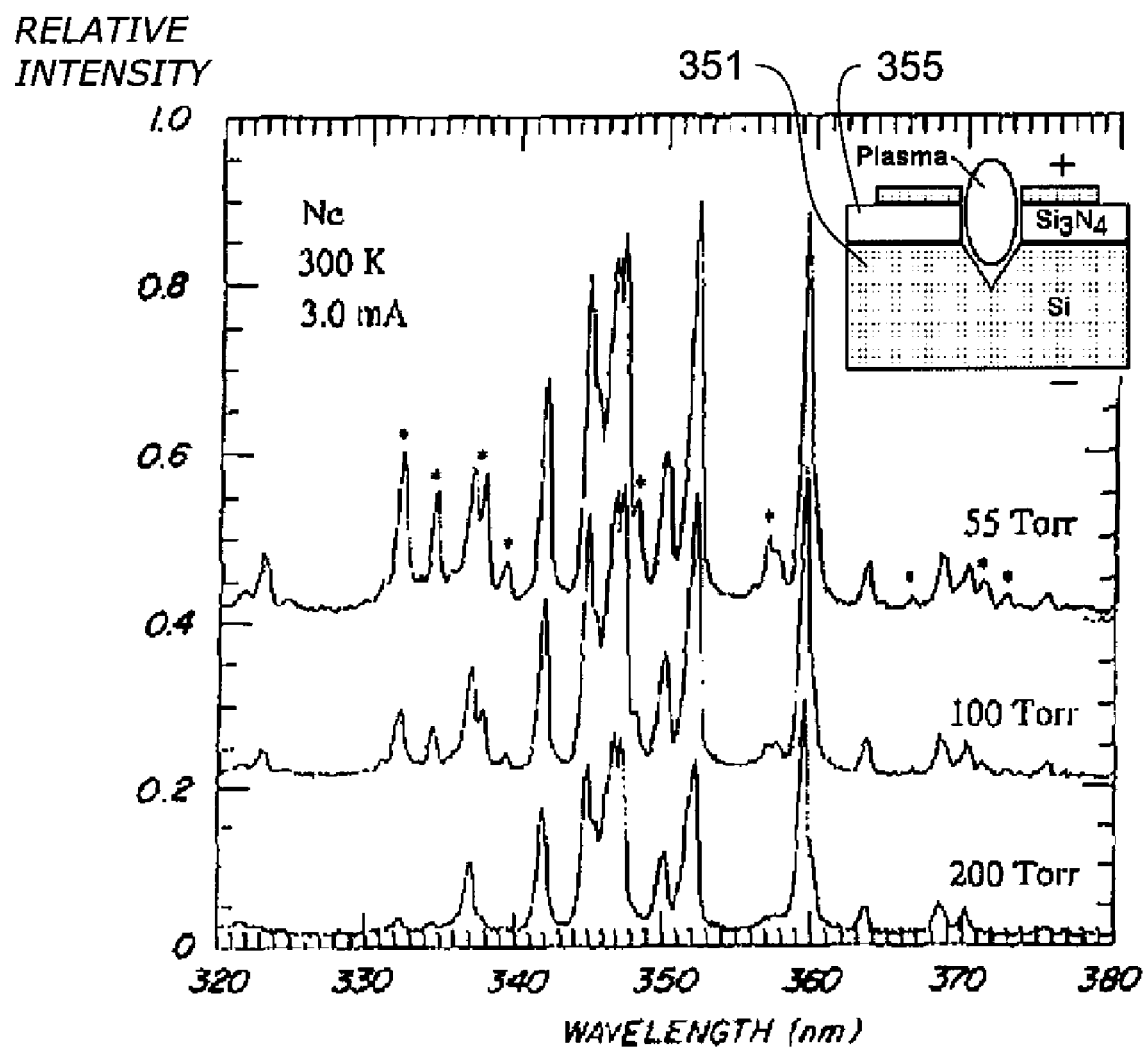
FIG. 12 is a graph of the relative intensity, discharge versus pressure for a gas.

An example of how the selective wavelength channels of an AED can identify the atomic makeup of a compound separated by GC is illustrated in FIG. 11, which shows separate channels for C, H, N, O, S, Cl, Br, P, D, Si and F atomic emissions, with a corresponding list of channels in the table of FIG. 10. FIG. 11 shows chromatograms of a multielement test mixture with various peaks that may indicate the element and its approximate amount. Peak 301 indicates 2.5 ng of 4-fluoroanisole; peak 302 indicates 2.6 ng of 1-bromohexane; peak 303 indicates 2.1 ng of tetraethylorthosilicate; peak 304 indicates 1.9 ng of n-perdeuterodecane; peak 305 indicates 2.7 ng of nitrobenzene; peak 306 indicates 2.4 ng of triethyl phosphate; peak 307 indicates 2.1 tert-butyl disulfide; peak 308 indicates 3.3 ng of 1,2,4-trichlorobenzene; peak 309 indicates 170 ng of n-dodecane; peak 310 indicates 17 ng of n-tridecane; and peak 311 indicates 5.1 ng of n-tetradecane. For such chromatograms, the GC conditions may include a column flow of 3.3 mL/min, a split ratio of 36:1, and an oven program from 60 degrees to 180 degrees Centigrade (C) at 30 degrees C./min. Part of a UV spectrum of neutral and ionized emitters of Ne, generated with low-power microdischarges are shown in FIG. 12. Also shown in this figure is that the spectral species change in intensity as the "Ne" pressure changes. The optical output may depend on several parameters such as discharge cavity geometry, applied voltage and pressure. Molecular bands are emitted and may even be used for "NO" measurements of such gases as in the hot exhaust of jet engines.

One may obtain useful gas composition information by feeding an environmental gas sample to microdischarge devices. In a first approach, one may use one microgas discharge device, the operating parameters (voltage, pressure, flow . . . and possibly the geometry) of which may be changed to yield variations in the output emission spectrum such that after evaluation and processing of such emission data, information on the type and concentration of the gas sample constituents may be made. In a second approach, one may use several micro-gas discharge devices, whereby the operating parameters of each may be changed, for emission output evaluation as in the first approach, and may obtain better results via a statistical analysis. The third approach may be the same as the first one, except that each micro-discharge may be only operated at one condition, but set to be different from that of the set-point of the other microdischarges.

Figure 13:
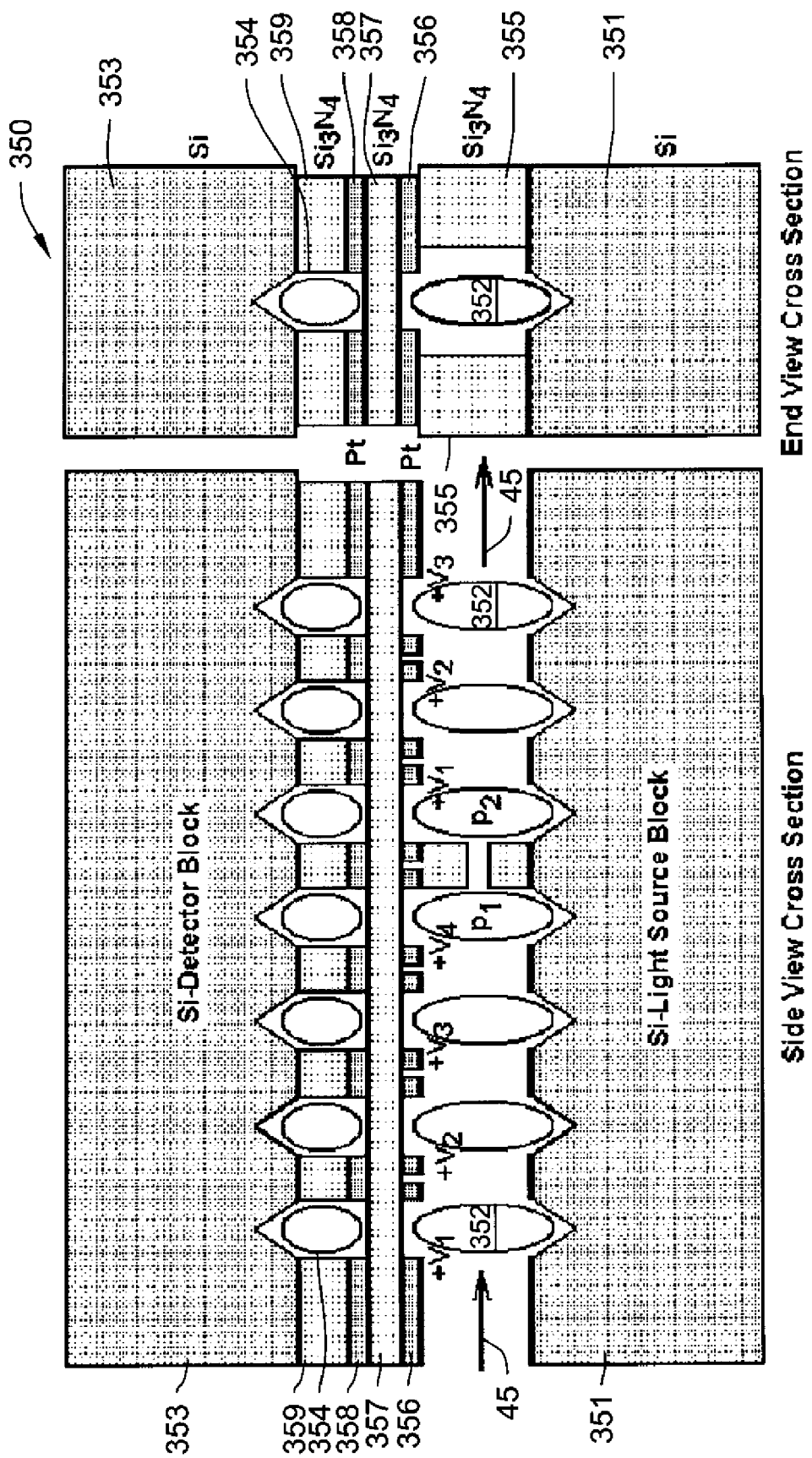
FIG. 13 shows sectional views of an array of light source and detector pairs for gas sensing.

FIG. 13 represents the third approach, whereby the gas sample may pass serially from one type of discharge to the next, and the assumption may be that the nature of the gas sample does not change during this process. The figure shows an array 350 of light source-detector pairs for gas composition sensing in a gas 45 stream at various pressures and voltages. The different voltages, +V1, +V2 . . . and pressures P1 and P2 may be marked as such. The plasma of the micro discharges 352 from the light source block 351 are indicated by the ellipsoids between the (+) and (−) electrodes. Opposing source block 351 is a detector block 353 having micro gas discharge devices operating as detectors 354 of the light from the source discharges 352. There may be filters situated on detectors 354. The filters may be different and selected for detection and analysis of particular groups of gases. The various lines of emission of the gases from the micro discharges may be detected and identified for determining the components of a detected gas. Array 350 may be connected to controller 130. A processor may be utilized in the control of the micro discharges and the detection of the effects of the discharges in the flow of gas 45 through array 350.

Light source block 351 may be made from silicon. Situated on block 351 may be a wall-like structure 355 of $Si_3N_4$ or Pyrex™ forming a channel for containing the flow of gas 45 through device 350. On top of structure 355 may be a conductive layer of Pt or Cu material 356. On the Pt material is a layer 357 of $Si_3N_4$ that may extend over the flow channel. On top of layer 357 may be a layer 358 of Pt and a layer 359 of $Si_3N_4$ as a wall for forming a channel for detectors 354. The fourth approach may be like the third approach except for the feeding the gas sample to each discharge in a parallel rather than serial fashion.

A fifth approach may be the same as the fourth or third approach, except that the gas sample may have undergone a separation process as provided, e.g., by a conventional GC. A sixth approach may be the same as the fifth approach, except that prior to the separation process, the sample analytes of interest may be first concentrated by a conventional preconcentration step.

The seventh approach may be the same as the sixth approach, except that prior to the separation process, the sample analytes of interest may have been previously concentrated by a multi-stage pre-concentration process and then electronically injected into the separator as offered by the phased heater array sensor.

In the sixth and seventh approaches with reference to FIG. 2, the idea is to feed individual gas-analyte peaks eluting from the GC column or the phased heater array sensor separator channel to each discharge device in the shown array of discharges.

Gas flow may be in series as shown in FIG. 13. Or it may be in parallel which may be necessary for an optimal peak identification, whereby (for the sake of minimizing total analysis time) each discharge cell may operate at a fixed condition of applied voltage, gas pressure (determined by the vacuum or suction pump at the exit of the array, e.g., by a Mesopump™). In FIG. 13, only two pressures may be indicated by way of example, as easily achieved by a flow restriction between the $4^{th}$ and $5^{th}$ discharge element. Several changes in the discharge parameter such as flow rate, temperature (via local micro-heaters) or geometry (hollow-cathode or flat-plate discharge, besides simple changes in the identification of cell) are not shown, but may be likewise implemented.

Due to their typically small size (10-100 μm), these sensors may not appear to use much real estate and may be included in block 128 of FIG. 2.

Sensor 15 may have a flow sensor 125 situated between concentrator 124 and separator 126, a thermal-conductivity detector at the input of concentrator 124. It may have a thermal-conductivity detector between concentrator 124 and separator 126. There may be a thermal-conductivity detector at the output of discharge mechanism 350. Sensor 15 may include various combinations of some of the noted components in various locations in the sensor 128 of FIG. 2, depending upon the desired application. The drawing of sensor 15 in FIG. 2 is an illustrative example of the sensor. Sensor 15 may have other configurations not illustrated in this figure.

Figure 14:
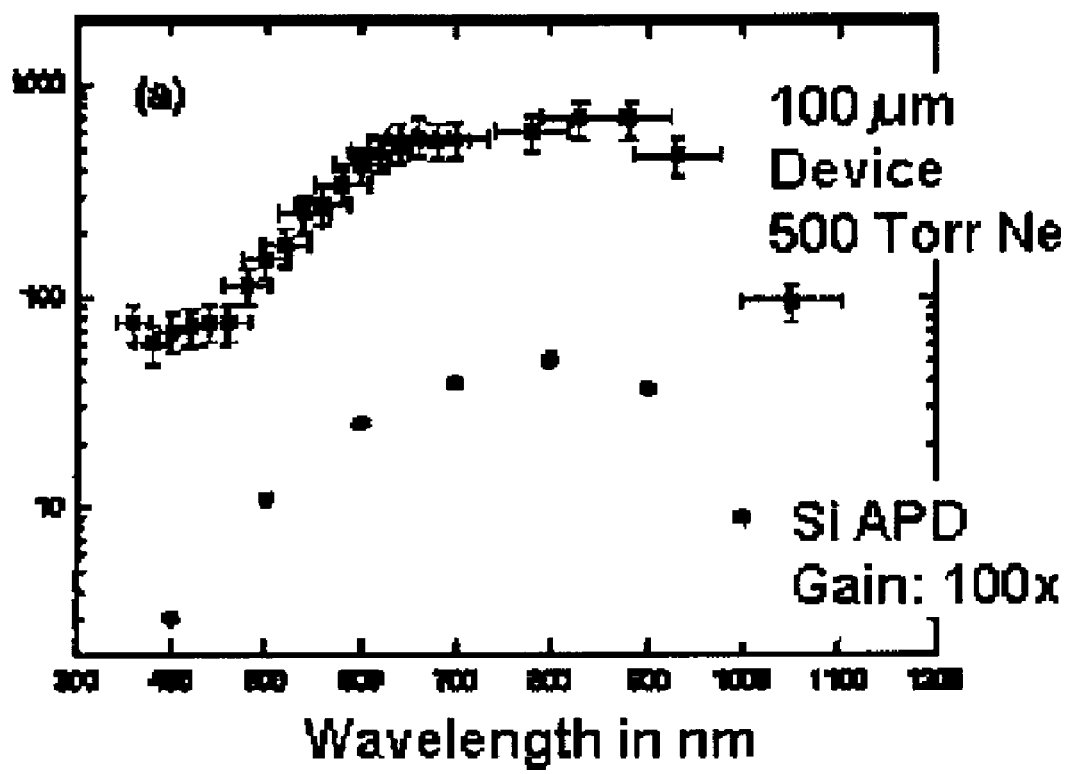
FIG. 14 is a graph of a spectral responsivity comparison between a micro discharge device and a Si-photo diode.

The gas micro-discharge cells may offer attractive features, which may significantly enhance the usefulness, versatility and value of the phased heater array sensor. Examples of the features include: 1) low power capability—each discharge operates at 700-900 Torr (0.92-1.18 bar) with as little as 120 V DC, at 10 μm, which may amount to 1.2 mW that appears to be a minimal power not even achieved by microTDCs; 2) ease of building along with a compactness (50×50 μm), shown the insert of FIG. 12; 3) the operability of micro-discharges as photo detectors which may be shown by the spectral responsivity comparison between a 100 μm micro-discharge and an Si APD in FIG. 14, which no other light sources such as 100-W microwave driven AEDs (requiring water cooling) are known to do; 4) the integratability and wafer level assembly of the discharge source and photodiodes with a phased heater array structure, without having to resort to Si-doping to manufacture monolithic Si-photodiodes; and 5) the added dimensionality (i.e., selectivity) by varying discharge parameters as noted above.

The present invention may have gas composition sensing capabilities via micro-discharge having: 1) a combination of phased heater array sensor with micro gas discharge devices; 2) the combination of 1), whereby one set or array of gas discharge devices may provide the spectral emission and another, complementary set (with or without narrow-band band-pass filters or micro spectrometer) may provide the light detection function; 3) the combination of 2) with appropriate permutations of designs described above under the first through seventh approaches; and 4) the flexibility to program heatable elements as additional pre-concentrator or additional separator elements of the phased heater array structure, as needed for a specific analysis, to achieve optimal preconcentration or separation performance.

The present phased heater array sensor-microdischarge detector combination over previously proposed micro gas analyzers may provide sensitivity, speed, portability and low power of the phased heater array sensor, combined with the selectivity, "peak-identification" capability, low-power, light source and detection capability, integratability, simplicity and compactness contributed by micro gas discharge devices, which no other microanalyzers have been known to achieve.

Figure 15:
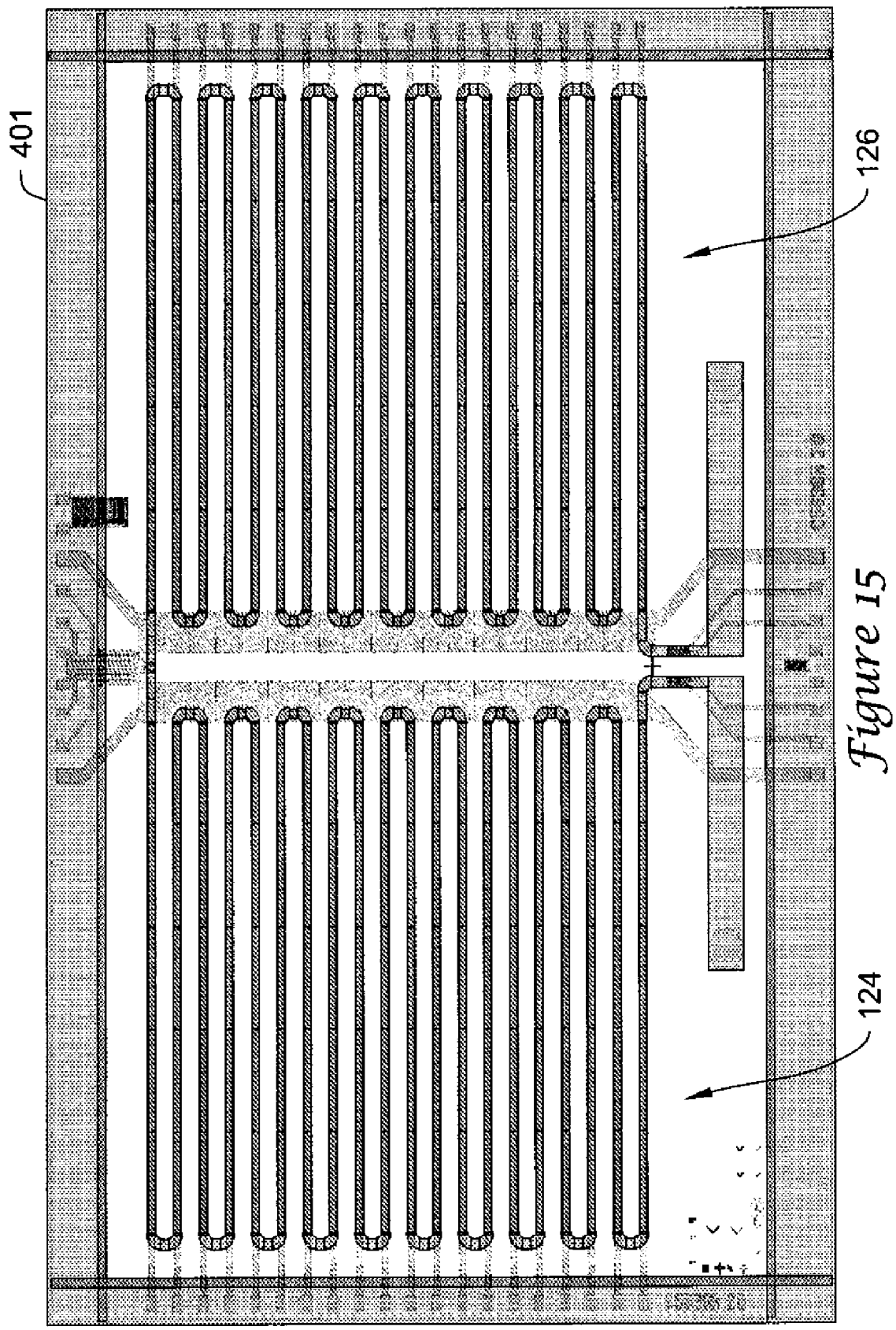
FIG. 15 is an illustration of an integrated layout for the phased heater array structure that includes sensors, a concentrator and a separator.

FIG. 15 illustrates the integration of sensors, pre-concentrator and/or concentrator 124 and separator 126 of micro gas apparatus 15 (i.e., the phased heater array structure) on a single chip 401 which would be mounted and connected on a circuit board that also connects with other chips as well. One such other chip may hold FET switches, shift registers and logic. The 401 chip may reside on a daughter board. The 401 chip and the main circuit board were originally connected by about 110 wires. However, after the integration of all of the switches onto the separate chip on the daughter board, the number of printed circuit board routing leads and connector pins was reduced to about 10 (i.e., for differential temperature compensation, flow sensor, switch clock, logic, power and ground). The FET switches, shift registers and control logic located on a separate IC may be connected to the phased heater array structure chip via wire-bonds or solder-bumps. With the new logic of the FETs, a user of sensor system 15 may select the fraction of total heatable elements for operating as pre-concentrators versus separators.

Figure 16:
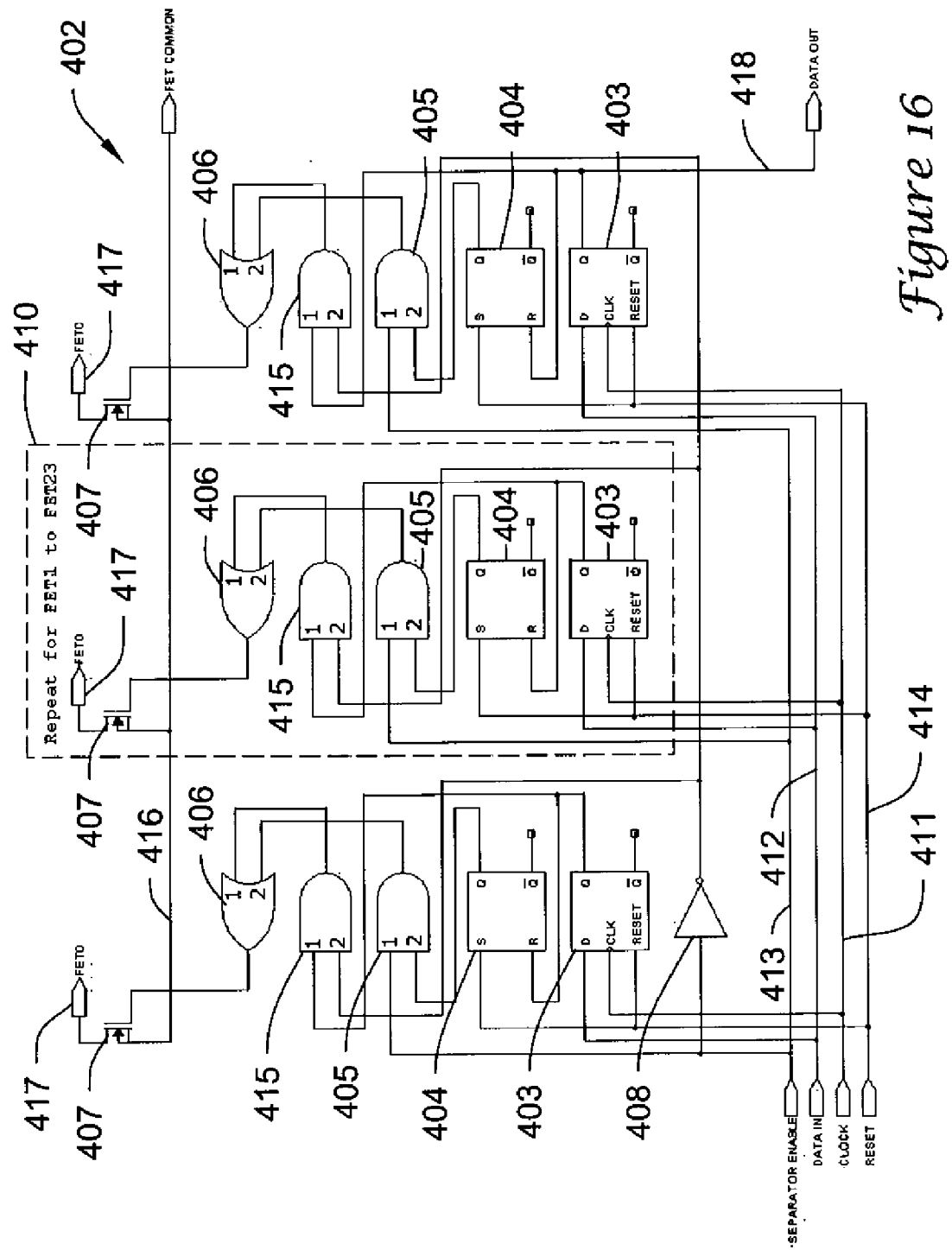
FIG. 16 is a schematic of the logic heating element selection for concentrator and separator portions of a sensor.

FIG. 16 is a schematic of an illustrative example 402 of control logic for sensor system 11. Circuit 410 may be an instance of a logic cell in an array. It may contain D flip-flops 403, R-S flip-flops 404, AND gates 405 and 415, OR gates 406, FETs 407 and an inverter 408, plus additional circuitry as needed. A clock line 411 may be connected to a clock input of D flip-flop 403. A separator enable line 413 may be connected to a first input of AND gate 405. A data-in line 412 may be connected to a D input of flip-flop 403. A reset line 414 may be connected to an S input of flip-flop 404 and a reset input of flip-flop 403. A Q output of flip-flop 404 may be connected to a second input of AND gate 405. A Q output of flip-flop 403 may be connected to an R input of flip-flop 404 and to a first input of AND gate 415. Separator enable line 413 may be connected to an input of inverter 408. An output of inverter 408 may be connected to a second input of AND gate 415. Outputs of AND gates 415 and 405 may be connected to first and second inputs, respectively, of OR gate 406. An output of OR gate 406 may be connected to a gate of FET 407. The other terminals of FET 407 may be connected to a FET common line 416 and a FET output terminal 417, respectfully. The far right logic cell may have a Q output of flip-flop 403 connected to a data out line 418.

This logic may allow the user to pre-select the number of pre-concentrator elements that the circuit will pulse and heat up, before pausing and then ramping up the temperature on all of the remaining heater elements, which then may function as part of the segmented separator. There is an additional dimension of flexibility which may allow for the depositing of different materials on any of the phased heater array sensor elements of chip 401 chip via suitable masking, so that preferential preconcentration, filtering of interference and cascaded separation may be enabled.

FIG. 16 further illustrates how up to 50 FET switches may be controlled by on-chip logic, each having an on resistance at or below 0.5 ohms and be able to switch about 12 volt potentials. The on-chip logic may operate in two modes, that is, the concentrator or $1^{st}$ mode and the separator or $2^{nd}$ mode, the respective mode being determined by a control line bit. The $1^{st}$ mode may involve a shift register which, after a reset, sequentially turns on a low resistance FET, and disables a flip-flop associated with that same FET. At the next clock cycle, the first FET turns off, and the next FET turns on and its associated flip-flop is disabled. This sequence may be repeated until some external drive electronics turns off the clock and enables the $2^{nd}$ operating mode. Once the second mode is enabled, all of the FETs where the flip-flop has not been disabled may turn on simultaneously. This $2^{nd}$ mode may stay on until the reset has been triggered and the flip-flops are reset, the FETs are turned off and the process can be repeated.

Two chips may be used in series to bond to the (up to 50) the phased heater array sensor chip pads on each of its sides, such that the sequential switching will go from the first chip to the second chip. It may be necessary for the signal from the last switch on the first chip to trigger the first switch on the second chip. It is possible that the mode switch from sequential addressing of the remaining FETs in parallel may happen sometime before or after the switching has moved to the second chip.

One may introduce adsorber coating diversity into the phased heater array sensor heater elements, such as by alternating individual elements or groups of elements in either or both pre-concentrator or the separator, with more than one adsorber material, and adjusting the logic program for the switches as in FIG. 16 or to favor (in terms of maximum applied voltage or temperature) certain types of coatings in the pre-concentrator and equally or differently in the separator, to achieve the desired analyte preconcentrating, analyte filtering and analysis results which may be the analysis of selected group pre-concentrator pulses or cascaded (in time) pre-concentrator analyte pulses.

The user may be enabled with great flexibility to adjust the phased heater array sensor operation and performance to the varying needs imposed by the analysis problem: He can select the number or fraction of total heater array elements to function as pre-concentrators vs. separators, thus varying the concentration of the analyte relative to the separation, i.e., resolution and selectivity of the analyte components, while retaining the ability to design and fabricate low-power, optimally temperature-controlled heater elements, that feature structural integrity, optimal focusing features, analyte selectivity/filtering, and smart integration of preconcentration, separation, flow control and detection technology, such as TC and micro-plasma-discharge sensors. One may integrate the CMOS drive electronics with the phased heater array sensor flow-channel chip.

In important gas analysis situations, such as when health-threatening toxins, chemical agents or process emissions need to be identified with little uncertainty (low probability for false positives) and quantified, conventional detectors and even spectrometers (MS, GC, or optical) cannot provide the desired low level of false positives probability, $P_{fp}$.

Combined analyzers such as in GC-MS and GC-GC systems may approach the desired low $P_{fp}$ values, but are typically not-portable desk-top systems, because of two sets of complex and bulky injection systems, bulky MS pumping systems and large amounts of energy needed for each analysis. Most importantly, the false positives probability rapidly increases if desktop or portable systems cannot provide the needed sensitivity, even if the separation capability is excellent.

Figure 17:
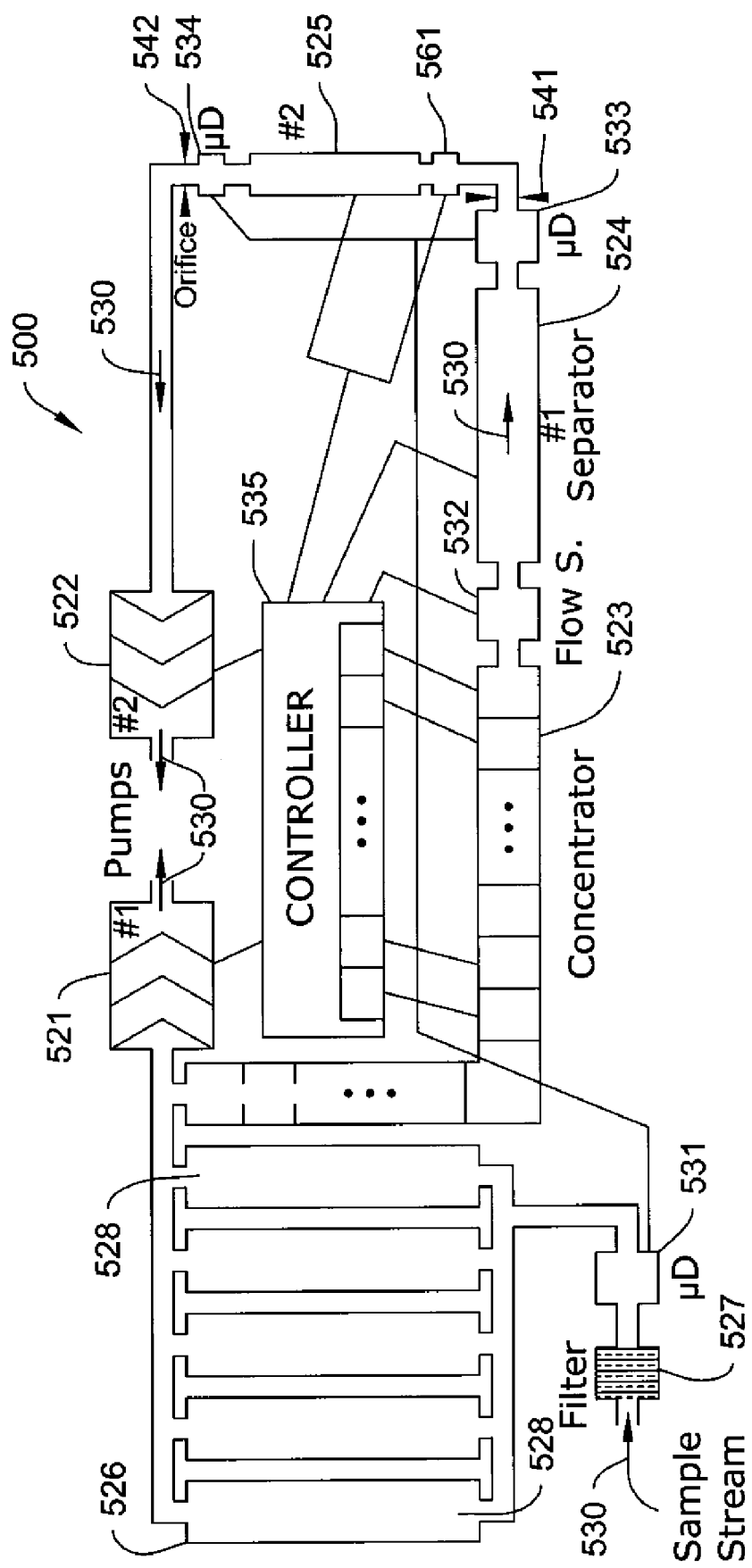
FIG. 17 shows a micro analyzer having a hyper pre-concentrator.

A solution is embodied in a micro analyzer 500 shown in FIG. 17, which may combine the selectivity provided by the μGC-μGC-like configuration if needed, that is, if not a simple micro gas chromatograph (μGC) would do, as well as the sensitivity afforded by the multi-level, multi-stage pre-concentration. In this configuration, micro analyzer 500 may still retain its (palm-top to cubic-inch type) compactness, 3-second analysis, ppb sensitivity, flexibility, smartness, integrated structure, low-power and low cost features. Another solution may be embodied in a micro analyzer 600 of FIG. 21.

Micro analyzer 500 may take in a sample stream of fluid 530 through an input to a filter 527. From filter 527, fluid 530 may go through a micro detector (μD) 531 on into a $1^{st}$-level pre-concentrator 526 having parallel channels 529. Fluid 530 may be drawn through channels 529 by pump 521 or by pump 522 through the main portion of micro analyzer 500. Pumps 521 and 522 may operate simultaneously or according to individual schedules. A portion of fluid 530 may go through concentrator 523 and on through flow sensor 532. Concentrator 523 may have an about 100 micron inside diameter. From flow sensor 532, fluid 530 may go through separator 524, micro detector 533, separator 525 and micro detector 534. Separators 524 and 525 may have inside diameters of about 140 microns and 70 microns, respectively. Fluid 530 may flow on to pump 522. Fluid 530 exiting from pumps 521 and 522 may be returned to the place that the fluid was initially drawn or to another place. Each of micro detectors 531, 533 and 534 may be a TCD, MDD, PID, CRD, MS or another kind of detector. Analyzer 500 may have more or fewer detectors than those shown. It may also have flow orifices, such as orifices 541 and 542 at the outlets of micro detectors 533 and 534, respectively. Analyzer 500 may also have valves and other components. A control device 535 or micro controller or processor may be connected to pumps 521 and 522, detectors 531, 533 and 534, sensor 532, concentrator 523, separators 524 and 525, and other components as necessary to adequately control and coordinate the operation of analyzer 500, which may be similar to that of a micro fluid analyzer described in the present description.

A feature of micro analyzer 500 may relate to the introduction of additional pre-concentration dimensions. Each of these supplies an enhanced analyte concentration to the subsequent pre-concentrator operation, as depicted schematically in FIG. 17. This is different from previously proposed and built single-level, multi-stage pre-concentrators (PC). In the multi-level PC system, the analyte concentration achieved in the $1^{st}$-level PC and presented for adsorption to the next or last-level (multi-element and multi-stage) pre-concentrator is already enhanced by the $1^{st}$-level pre-concentrator, and this previous pre-concentrator needs to be large enough to be able to release analyte for the time period needed for about full operation of the $2^{nd}$-level or last pre-concentrator.

Assuming that the volumetric ratios of mobile phase over stationary phase and the ratio of partition functions at adsorption and desorption temperatures is such that G=100-fold concentration gains can be achieved for a hypothetical analyte, then the timing of increasing concentration levels is as indicated by the sequence of numbers 511, 512, 513, 514, 515 and 516 in FIG. 18 as follows (it helps to remember that for gas diffusion to evenly re-distribute removed or desorbed gas in a square cross section channel of side, d=0.01 cm only takes a time of $\Delta t = d^2/(2D) = 0.01^2/2/0.1 = 0.0005$ seconds).

The multi-level PC operation may be described as going through a sequence of steps: 1) Adsorption time, $z_a$. Analyte of mol fraction X=1 ppt flows with the sample gas at v=110 cm/s, for sufficient time, $z_a$, to equilibrate with the stationary phase: $z_a = N_1 GL/v$, where $N_1$ = number of adsorbing elements, L=length of adsorbing film element in the flow direction. For $N_1$=500 and L=0.5 cm one may get z=500×100×0.5/110=227 seconds. Note that $z_a$ is independent of X, provided X is small relative to 1 even after all pre-concentration steps are completed. (For chips with $N_1$=50, the time would be 22.7 seconds, for chips with L=0.1, this time could be 4.3 seconds. Increasing the sample gas flow velocity would decrease this time, but increasing the film thickness would increase that time).

2) Saturation. At the end of the time, $z=z_a$, the first-stage adsorber is largely saturated (one may ignore here for clarity's sake, the exponential nature of the diffusional mass transfer from the sample gas to the stationary film), while the sample gas continues to flow with analyte concentration, x, as indicated by the dashed line. In FIG. 18, this is indicated by concentration regions 511 and 512 for the gas and stationary phases, respectively.

3) 1st-Level Desorption Start. At any time $z \geq z_a$, e.g., $z=z_o$, one may rapidly (within 1 ms) heat all $N_1$ elements, which then fill the sample gas channel with a 100× higher concentration, i.e., x=100 ppt (see region 513 in FIG. 18). As the "plug" of this 100-fold enriched sample gas enters the first element of the next level PC, $N_2$, it will try to equilibrate and saturate the next set of $N_1/G$ adsorber elements of $N_2$ with a 100× higher analyte concentration (region 514 in FIG. 18) than in the previous region 512.

4) 2nd-Level Adsorption Time Period. One may only have available a finite time and finite plug or column of gas moving at a velocity, v, to do this, before unconcentrated sample gas purges the concentrated analyte out of region 514 in FIG. 18. The available time $z \approx N_1 L/v = z_d/G$, or 2.27 seconds, for the above but arbitrary example with $N_1$=500, L=0.5 cm and v=110 cm/s.

5) 2nd-Level Desorption Time Start. The second desorption should start no later than at $z=z_o+z_d/G$, by heating only the first of the $N_2$ elements, for a time $\Delta z$=L/v, which may be between 1 and 5 ms (in the example, $\Delta z$=4.5 ms). This may generate and raise the analyte concentration in the channel (region 515 in FIG. 18) 10,000-fold, relative to the original x-value. When the time $\Delta z$ has passed, the second element may be heated, and so on, until all $N_2=N_1/G$ elements have been pulsed, and thus added their desorbed analyte to the passing gas. The time needed to do this may be $\Sigma(\Delta z)=\Delta z \cdot N_2 = (N_1/G)(L/v)=z_d/G^2$ or $227/10^4$=23 ms, for an arbitrary example with $N_1$=500, $N_2=N_1/G$=5, L=0.5 cm and v=110 cm/s.

6) 2nd-Level Desorption Time Period. The final analyte concentration exiting this pre-concentrator at region 516 in FIG. 18 may be $x=x_o G^2 N_2 = x_o N_1 G$=50,000, i.e., a 50,000-fold increase over the starting analyte concentration in the sample gas. This may be a ~10× higher pre-concentration gain than achieved when the source analyte was adsorbed only once and concentrated with only one set of phased elements.

Figures 18, 19:
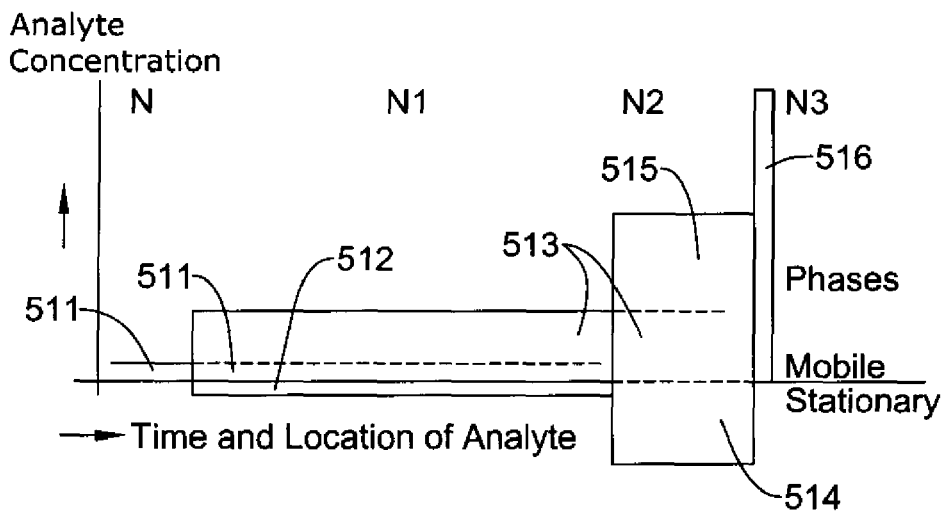
FIG. 18 is a diagram revealing analyte concentration levels at various pre-concentration phases and times.
FIG. 19 is a table of a number of elements and respective concentration gains.

The example with $N_1$=500 used above was entered as row A in the table of FIG. 19. Rows B-E list additional examples with increasing number of elements and correspondingly larger total concentration gains achieved. However, the pressure drop through a typical MEMS channel of 100×100 μm in cross section increases rapidly as we increase the number of elements, as shown in the table of FIG. 20. For just $N_1$=50, v=100 cm/s and L=0.5 cm, one may get $\Delta p$=2.6 psid, with air as the main component in the sample gas. The $\Delta p$ for $N_1+N_2$=505 or 1010-element pre-concentrators may rapidly become impracticably large, even if each element is shortened to L=0.1 cm, as shown via the pressure drops and peak power data computed and listed in FIG. 20, showing $\Delta p$ values of 5.3 and 10.6 psi, respectively. One way to alleviate this high-pressure drop, which is especially undesirable for systems in which the sample is drawn through via a suction pump, is by setting up the $N_1$ elements in two or more equal and parallel channels. For q parallel channels, the pressure drop may fall to $\Delta p/q$, without changing the soaking time or the needed peak power, because desorption of all the parallel elements of $N_1$ needs to be occurring simultaneously, unless each channel is provided with suitable valving, so that they can be desorbed sequentially. Preferably, the soaking time could be reduced by this scheme of parallel channels, without valves, by using the two-pumps 521 and 522, as illustrated in FIG. 17.

While both pumps 521 and 522 may draw sample gas during the soaking period, the flow through micro analyzer 500 may be unaffected due to the stronger vacuum of its pump 522, but may allow a 1st-level pre-concentrator 526 to draw 10-100× larger flow rates with its pump 521 and thus complete this soaking period in a 10-100× less time. After the end of the soaking period, one may stop pump 521 and let pump 522 draw sample gas through both concentrator 523 and separators 524 and 525 of micro analyzer 500 and added pre-concentrator 526 with parallel channels 529.

Hyper pre-concentrator 526, concentrator 523 and concentrator 623 may have channels which include heater elements 20, 22, 24, 26 and so on with interactive elements 40, 42, 44 and 46 and so on, and alternatively with additional interactive elements 140, 142, 144, 146 and so on, as in FIGS. 3-5. Controller 535 and 635 may be electrically connected to each of the heater elements 20, 22, 24, 26. Controller 535 and 635 may energize heater elements 20, 22, 24, and 26 in a time phased sequence (see bottom of FIG. 7) such that each of the corresponding interactive elements 40, 42, 44, and 46 become heated and desorb selected constituents into a streaming sample fluid 530 and 630 at about the time when an upstream concentration pulse, produced by one or more upstream interactive elements, reaches the interactive element. Any number of interactive elements may be used to achieve the desired concentration of constituent gases in the concentration pulse.

Features of micro analyzer 500 may include: 1) Integrating into other micro analyzers the approach to perform multi-level, multi-stage pre-concentration; 2) Having such approaches accomplished with two pumps, as in micro analyzer 500, except that the purpose for the low-pressure pump was then to simply accelerate the filter purge rate, while here one may take advantage of it as a way to reduce the 1st-level pre-concentrator soak time; 3) Performing the 1st-level pre-concentration in such a way that its output can serve briefly as a higher concentration analyte source for the 2nd-level pre-concentrator, which may be of the multi-stage type; 4) In cases requiring extreme sensitivity (e.g., for analytes present in sub-ppt levels), performing the 1st-level pre-concentration in such a way that its output may serve briefly as a higher concentration analyte source for the 2nd-level pre-concentrator, which in turn may serve as a higher concentration analyte source for the 3rd-level pre-concentrator, which may be of the multi-stage type; 5) A 1st-level pre-concentrator that is not simply a very long channel (~100× longer than previously disclosed multi-stage pre-concentrators, if G=100 is the concentration gain achievable at each adsorption-desorption stage) to serve as 100× higher concentration analyte saturation source for the final pre-concentrator level, which may result in a far too high a pressure drop, but one that consists of several channels in parallel to achieve a pressure drop that is much lower than that of the final pre-concentration level; 6) Achieving that low pressure drop by widening the pre-concentration channels, heaters and adsorber films without sacrificing desirably low volumetric ratios of gas/stationary phases; 7) Achieving that low pressure drop by increasing the thickness of the adsorber film, without unduly increasing the desorption time but decreasing desirably low volumetric ratios of gas/stationary phases; and 8) Being able to operate micro analyzer 500 structure in a flexible way, e.g., to meet the requirements for low-sensitivity analyses without operating the parallel 1st-level pre-concentrators, and/or without the second separator (μGC #2) if such ultimate separation is not required.

GC #1 and GC #2 may refer first and second fluid or gas chromatographs, respectively, of a micro analyzer. The first and second separators, which may be regarded as columns #1 and #2, respectively, may be a part of GC #1 and GC #2, respectively, along with the other components of the micro analyzer.

The advantages of micro analyzer 500 may include: 1) Very short analysis time (due to thin-film-based stationary film support) for μGCs of such selectivity, peak capacity and sensitivity; 2) Achieving the highest-possible sensitivities (due to very high PC levels) without compromising selectivity or analysis speed; and 3) Simultaneous achievement of the highest-possible sensitivity, selectivity and low energy-per-analysis capabilities (by virtue of using two separate pumps for the low-pressure purge and soak function, and a higher pressure one for the final pre-concentration level and separation functions).

Figure 21:
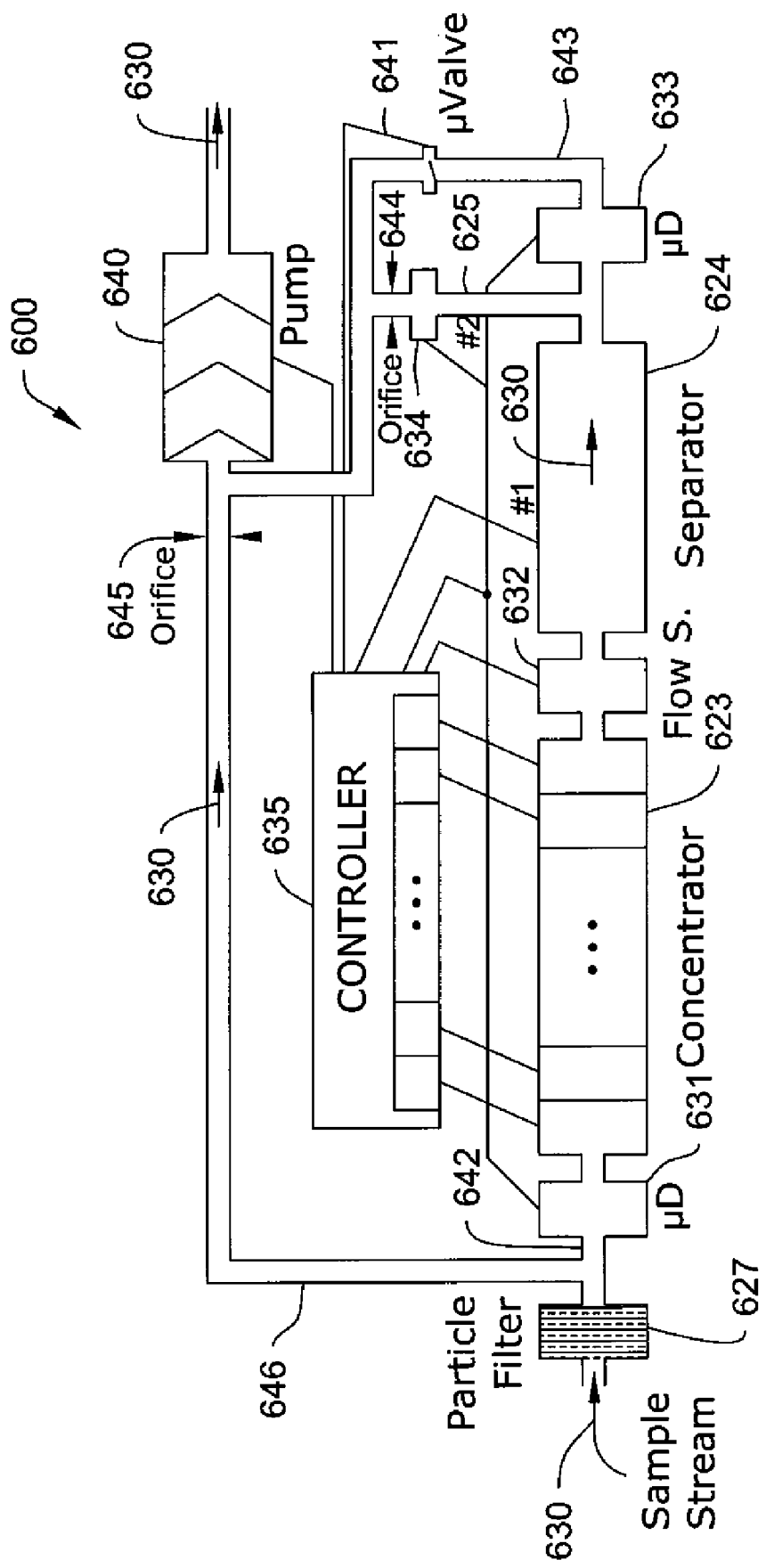
FIG. 21 is a diagram of a micro analyzer having a double gas chromograph configuration.

FIG. 21 shows a micro analyzer 600 having a GC-GC type two-dimensional structure. A sample gas stream 630, which may also serve as a carrier gas, may enter an input of a particle filter 627 and be pumped by pump 640 via two parallel channels. In the main channel, fluid 630 may proceed through a micro detector 631 and concentrator 623, respectively. Concentrator 623 may have an about 100 micron diameter. Fluid 630 may flow from concentrator 623 through a flow sensor 632 and into a separator 624, which may have an about 100 micron inside diameter. From separator 624, fluid 630 may split to flow through a second separator 625 and a micro detector 633. Separator 625 may have an about 50 micron inside diameter. The fluid 630 output from separator 625 may go through a micro detector 634 and an orifice 644. The fluid 630 output from micro detector 633 may go through a micro valve 641 via line 643. The flow of fluid 630 from a "T" connection at the output of filter 627 pumped through line 646 may be controlled by orifice 645. Control, microcontroller or processor 635 may connected to pump 640, micro detectors 631, 633 and 634, flow sensor 632, concentrator 623, separators 624 and 625 and micro valve 641 to effect appropriate operation of analyzer 600. Each of micro detectors 631, 633 and 634 may be a TCD, MDD, PID, ECD or another kind of detector. Analyzer 600 may have more or fewer detectors than those shown. It may also have additional valves and other components. In other approaches, micro valve 641 may be eliminated, so that only an uncontrolled pump and critical-orifice flow regulation remains.

The main channel is disclosed in the present specification and the second channel, embodying the second μGC, is "sampling" the emerging and relatively broad (half-width of μGC #1 peaks~total "free" elution time, $t_o$, of μGC #2).

What cannot be separated via a micro fluid analyzer structure entailing two or more separation film materials built into its integrated structure, may be realized here with an expanded, classical GC-GC structure. A relatively slow-moving 1st GC may generate peaks with a half-width of 10-30 ms, which may get analyzed by a pulsed 2nd GC every 20-100 ms, either on a timed or on a demand basis triggered by a detector at the end of that 1st GC. The second GC may additionally focus the inlet peaks via rapid (~1 ms) heating and cooling of its first heater element, so that its electronically- or micro valve-controlled injection peaks have a half-width of no more than ~1 ms.

In approach #1, analyzer 600 of FIG. 21, the flow of μGC #1 may be controlled by an active micro-valve 641, while flows through the bypass and column #2 may be controlled, i.e. set, by fixed orifices such as 634 and 645. In approach #2, micro valve 641 may be replaced by an additional, fixed orifice flow control.

Figure 22:
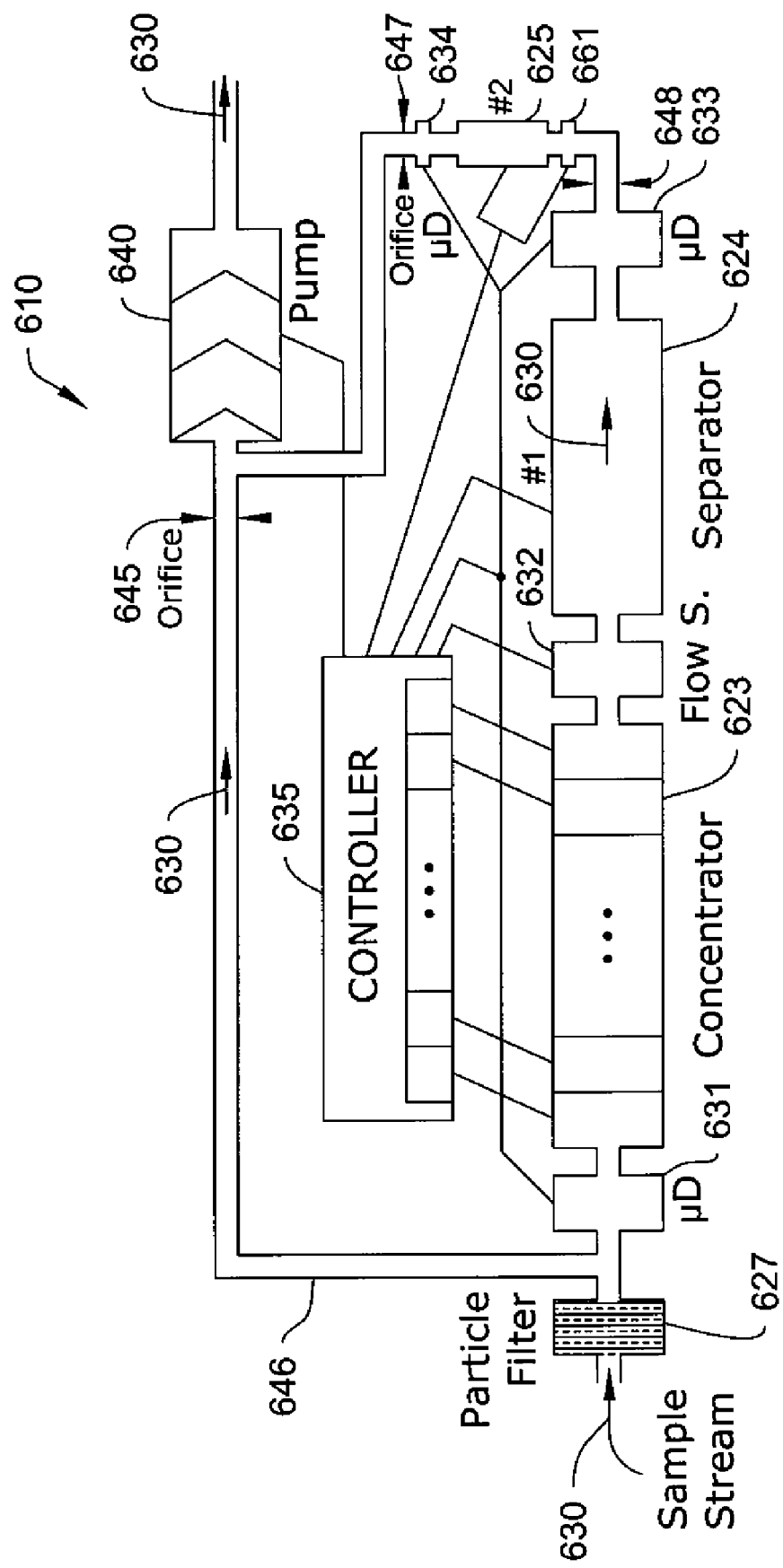
FIG. 22 is a diagram of a micro analyzer with a double gas chromograph having a bypass around the second separator.

In approach #3, all of the fluid 630 flow of μGC #1 may flow into μGC #2; the flow may be controlled by one fixed orifice 647 before pump 640 (of high but uncontrolled speed), and automatically accelerated upon transitioning to the cross section of column #2, after another fixed orifice/restriction 648 if needed, see FIG. 22.

Figure 23:
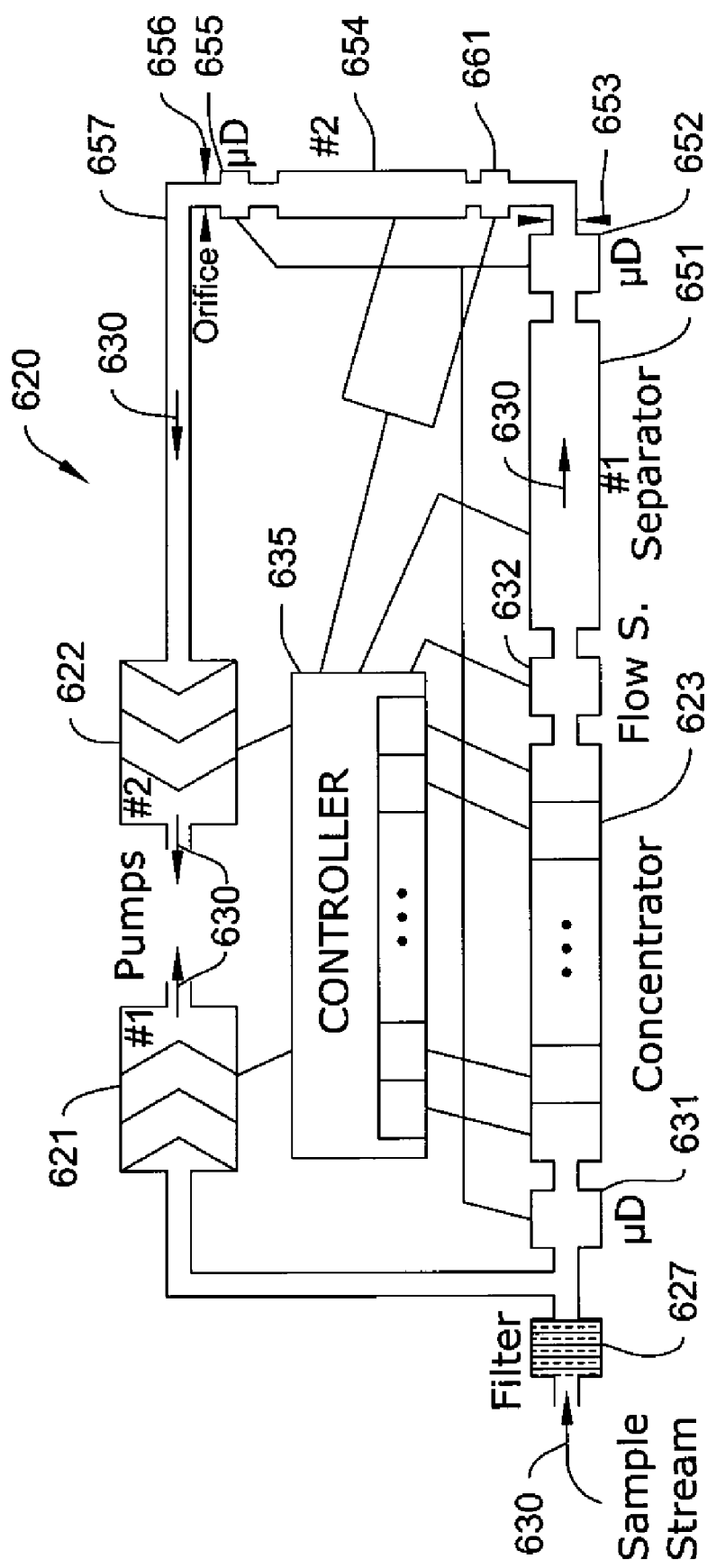
FIG. 23 is a diagram of a micro analyzer having a dual gas chromatograph configuration with two pumps.

FIG. 23 shows a micro analyzer 620 having two pumps 621 and 622 for better pumping of fluid 630. Adjacent to flow sensor 632 may be a separator 651 having an about 140 micron inside diameter. Flow 630 from separator may go through a micro detector 652, a micro detector 652 and an orifice 653, respectively. From orifice 653, fluid 630 may go through a separator 654 having an about 70 micron inside diameter. From separator 654, fluid 630 may go through a micro detector, an orifice 656 and line 657, respectively, and onto pump 622. Optionally, there may be a micro valve 561, 661 connected to separator 525, 625 and 654 of analyzer 500, 610 and 620, respectively.

In all cases, the broad peak being sampled may be "injected" into μGC #2 via and after a brief focusing period with the help of a short 1st adsorption element in the μGC #2 column, preferably made with stationary phase film material and the thickness of column #1. Its subsequent rapid heating and desorption may be used to inject that analyte into μGC #2, which may feature a narrower column, higher velocity and thinner adsorption film to approach the higher optimal velocity for maximum resolution of μGC #2. That higher velocity may also be implemented by the lower pressure in that column, either via the large pressure drop throughout the column #2 or via a fixed orifice (not shown in FIG. 21) at the junction between the end of above element #1 of column #2 and the remainder of column #2 or at the junction between columns #1 and #2.

During operation, the focusing process may be repeated either at fixed time intervals or only when column #1 detector senses a peak. Such a focusing operation may then start with a sharp drop in the temperature of that 1st element of column #2, for a period of typical 2×Δt the peak half-widths, e.g., 2×20 ms (see the table 1 in FIG. 24). After such a concentration period, $t_c$, the adsorbed analyte may be rapidly released, to result in peak half-width of about 2 ms. Other features of the exemplary data listed in FIG. 24 include the flow rates of sample gas in columns #1 and #2, V, which may need to be equal, for approach #3; the concentration time, $t_c=t_o(\#2)=2\Delta t$ (#1); the velocity of the sample gas, v, may need to be close to the optimal one to maximize the resolution, $R=t_R/\Delta t$, for a middle range of $0 \leq k \leq 5$, with $k=(t_R-t_o)/t_o$; and the time for desorption off the 1st element of column #2 (or last element of column #1), ~Δt/2, may need to be compatible with the local flow velocity, so that $l/v \leq \Delta t(\#2) \leq 2\ l/v$.

The probability of false positives may be reduced because the number of independent measurements (i.e., resolvable peaks, or total peak capacity) may be much larger with a μGC-μGC-μD, especially if the μD is a multi-channel detector such as a MDD, μECD, μFD (micro fluorescent detector). If the total peak capacity of μGC #1 is ~50, that of μGC #2 is ~30 and that of an MDD is ~10, the total number of independent measurement may be 50×30×10=15,000.

Features of micro analyzers 600, 610 and/or 620 may include: 1) An integration of a multi-stage pre-concentrator (PC)-μGC-μGC-detector on one chip, with options of further integration of additional detectors, and possibly more importantly the use of an optimal mix and synergy of materials for the PC, GC #1 and GC #2 films and the micro detector, μD, so that interferents that the μD is sensitive to are not retained and/or not pre-concentrated, but targeted analytes get pre-concentrated and well separated; 2) A smart and flexible operation of one or both μGCs of the present micro analyzer, e.g., with a user selection of the number or fraction of total heater array elements to function as pre-concentrators (PC) vs. separators (S), and/or with user-selection of the type of compounds chosen and desorbed from which pre-concentrator material (as opposed to desorbing all materials from various pre-concentrator elements); 3) A design of item 1) of this paragraph that retains its (palm-top to cubic-inch type) compactness, 3-second analysis, ≦ppb sensitivity, flexibility, smartness, integrated structure, low-power, valve-less electronic injection and overall low-cost feature; 4) A design of items 1) and 3) of this paragraph, whereby the shown and active micro valve 641 in FIG. 21 may be eliminated, so that only an uncontrolled pump and critical-orifice may remain for flow regulation; 5) A design according to items 1 through 4 of this paragraph, whereby the mass flow rates through μGC #1 and #2 may be equal, but these columns (and fixed pressure drop orifice or nozzle at the end of column #1) may be configured (ID, pump capacity and other fixed orifices to control pump speed through a sonic nozzle) to raise the flow speed by ~3-10× the level of column #1, to enable an approximately complete (within a time of about $t_o$ to $2t_o$) analysis to be done by column #2 within the time of the half-width of the peaks eluting from column #1, and may feature an adjusted adsorber film thicknesses, to optimally meet the values for Golay's equation; 6) Achieving operation of micro analyzer 600, 610 and/or 610 by "focusing" a complete peak from column #1 (see FIG. 24, Δt=20 ms) within a suitable (same or preferably ~half-sized) element, and a time of 2Δt, so it can be desorbed and flushed within a time, Δt2 ~1-2 ms; 7) The use of two pumps, 621 and 622 in FIG. 23, each designed for pumping at a particular flow rate and suction pressure, rather using one pump that may have to both satisfy the largest mass flow, pumping time and pressure requirement of the two tasks; 8) The integration and use of many types of integrated detectors, to reduce the probability of false positives, which decreases as one may increase the number of independent measurements, preferably by embedding of two separate functions into the micro analyzer—selectivity (via a spectrometric function, e.g., to separate analytes on the basis of their optical absorption, mass, boiling point, etc. properties) and sensitivity via a non-selective but very sensitive detector.

Advantages of the micro analyzer approach #3 may include: 1) A μGC-μGC combination to enable greater resolution and thus more complete analysis for a marginal increase in cost for the extra mask and deposition of a different adsorber film material; 2) A cost reduction based on eliminating an active valve and managing proper synchronization via small adjustments in the electronically controlled rate of the "heater-wave" propagation; 3) A further cost reduction due to a reduction in the calibration accuracy previously needed for the flow sensor (the flow may be roughly measured and adjusted with the aid of this flow sensor, but the optimal synchronization may be accomplished as described in item #2 of this paragraph) via electronic adjustment of the heater rate; 4) A further cost and maintenance reduction by using a pump capacity 20-80% higher than needed (at the same cost), but saving the control design and debugging effort involved with pump rate control (the excess capacity may be simply controlled via the flow limited by the fixed orifices); 5) The use of two pumps 621 and 622 as in FIG. 23, each designed for its task, is more efficient than using one pump that has to both satisfy the largest flow rate, pumping time and pressure requirement, and can save the cost and design effort of an additional orifice; and 6) The contribution of each $n_i$ in the system composed of the m-chain of elements PC-μGC-μGC-μD3 ... μDm may help minimize the probability of false positives, $P_{fp}$, where $$1/P_{fp} = [1 - \exp\{-(R_{SN}-1)/4\}](n_1, n_2, \ldots n_m)^{0.8}(Y+1),$$

and $R_{SN}$=signal/noise ratio, $n_1, n_2, n_3, \ldots n_m$=the number of independent measurements or elimination criteria (e.g., filtering steps via selective PC elements, spectrometric resolution elements via μGC #1 and μGC #2 or measurement channels via each of several different $\mu D_j$) and Y=1/P, the inverse probability that a particular false positive, once registered, can be confirmed as such via redundant sensors, repeat measurements, neighboring sensors in a sensor grid, and/or an occurrence of appearances of interferents of unusually high cross sensitivity.

Figure 25:
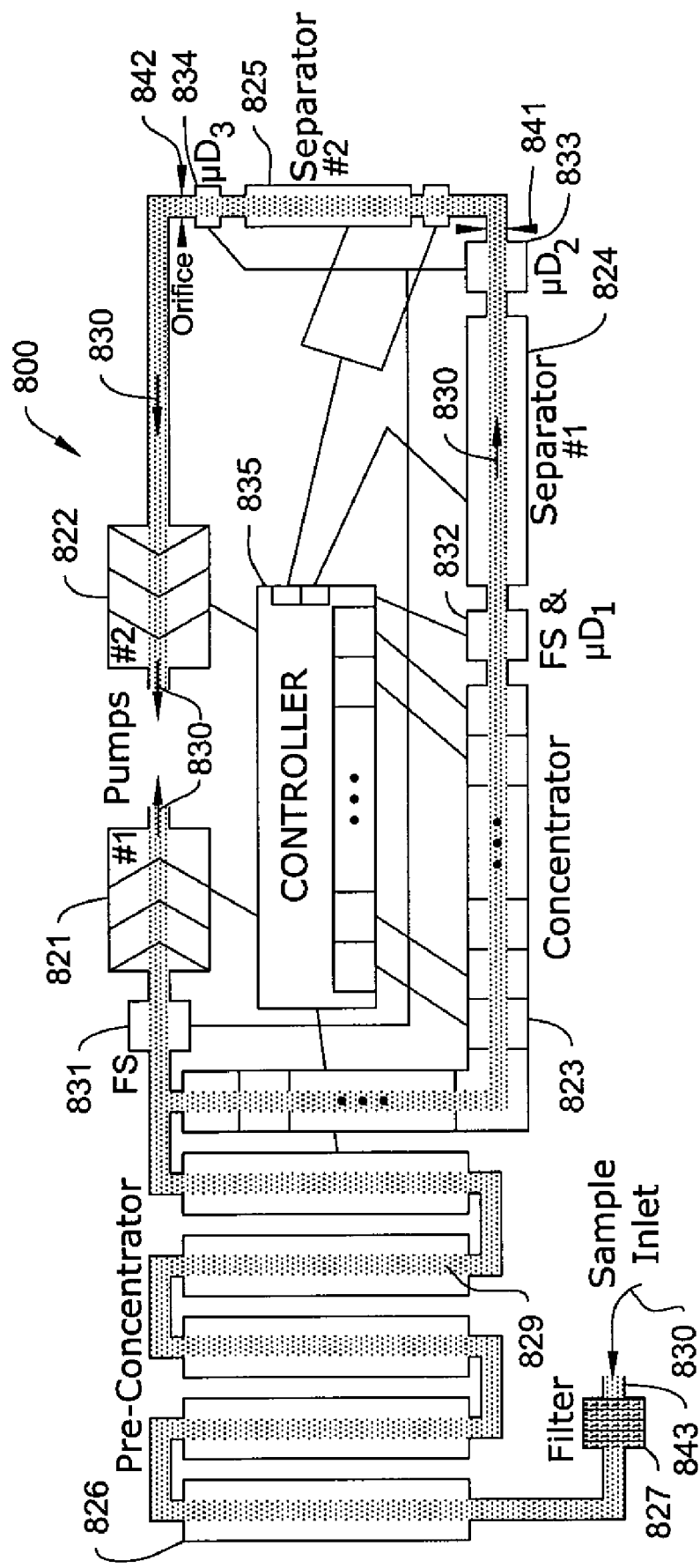
FIGS. 25 and 25a is a diagram of a micro analyzer having a two-stage concentrator and separator.

A micro analyzer 800 of FIG. 25, under combined maximum constraints of space, sensitivity, speed, energy-conservation and false alarms, such as for operation with battery power in unmanned aerial vehicles (UAVs), unattended ground sensors (UGSs), or out-patient monitoring, previous MGA (micro gas analyzer), may be compact enough, sensitive, fast, low-power and reliable enough to achieve performance goals for such functions. Analyzer 800 may have a sensitivity of ≦1 ppt (parts-per-trillion), total analysis time of ≦4 seconds, a use of less than 1 Joule of energy per analysis, and with a reliability exceeding that of desk-top GC-MS systems. All of this analytical power may be contained in about 2 cm³ of space (not including battery space) and meet or exceed the probability of false positives presently only provided by desk-top GC-MS analyzers. Although the sensitivity may be relaxed to less than 100 parts per trillion, the time per analysis to less than 50 seconds, and the energy used per analysis to less than 10 Joules. However, alternatively, the energy used per analysis may be less than 3 Joules at a time of less than 5 seconds with a detection limit near to 1.00 part-per-trillion. A concentration, separation, detection and analysis of a fluid may also mean that of analytes or constituents of the fluid.

An addition of a Lucent™ 1 to 10 micron ion-trap mass spectrometer to the micro analyzer 800 may make it a revolutionary small MS for vastly improved GC peak identification without the traditional penalty of requiring large costs, size and power needed for an associated vacuum pump.

Micro analyzer 800 may have structure, performance, and features as disclosed by information in various portions of the present description. Analyzer 800 may be useful as a very compact device for highly sensitive fluid detection and analysis. Analyzer 800 may be battery-powered in addition to its miniature and portable properties. However, analyzer 800, with certain the design features disclosed herein, may be regarded as consuming very small amounts of power thereby making it a very practical battery-powered analyzer.

Micro analyzer 800 may include power reduction characteristics. They may include analysis features such as optimal film thickness for pre-concentration (PC) and chromatographic separation (CS), improved heater element timing on PC and CS elements, incorporation of MDIDs (micro discharge impedance detectors), and other detectors and/or ITMS (e.g., ion trap mass spectrometer) and ASICs (application-specific integrated circuits). The mass spectrometer may instead be a time-of-flight, magnetic deflection or quadrupole type.

The terms "pre-concentrator" and "concentrator" may be used interchangeably in the present description. Device 826 may be regarded as a pre-concentrator, a first-level pre-concentrator, or a first level concentrator. Device 823 may be regarded as another pre-concentrator, second-level pre-concentrator, a second level concentrator, or just a concentrator. The "pre" may be an abbreviated term for "pre-analysis". FIG. 25 regards devices 826 and 823 as a pre-concentrator and a concentrator, respectively. One may refer to devices 826 and 823 as concentrators in general. (I do not understand "SOME KIND") Pre-concentrator 826 may have phased heaters that are timed with the passing gas analyte, with the heat pulse from the heaters moving at the same speed as the analyte. That is, the heaters may be turned on and off at a very short duration thus providing a heat pulse which moves along with the lump of gas or analyte as it moves through the concentrators, particularly the second concentrator 823. The heat in the moving gas is pulse-like in that it is cumulative and increases in temperature as the gas moves through the concentrator. The window of heating may be in a 5 to 6 millisecond range but may be kept as short as possible to conserve energy. The heated lump or "pulse" of gas or analyte may be prepped by the first concentrator for the entering the second concentrator that may have more stages (i.e., phased heaters) than the first one. The heat pulses in the second concentrator may be very short and sharp, and quickly can heat up an adsorbed gas or analyte to a high temperature. The more significant concentration increase of the gas tends to be in the second level concentrator. The first-level concentrator may ready, i.e., concentrate the gas for the second-level concentrator. In both concentrators, the phased heaters are off outside before and after the pulse of heater and the coinciding lump of heated gas or analyte as the latter moves through the respective concentrator. If there are for example 20 heater elements with each one being on for a period of 6 milliseconds, then the time of the heating of the flow of the gas or analyte may be about 120 milliseconds. Although the total time may be greater in that the concentrator may have hundreds or more phased heating elements. Interactive elements may be adsorber films deposited on the phased heater elements. The adsorber coatings may be of one, two or more compositions, where each type of coating adsorbs a subgroup of analytes and lacks interaction with the analytes not in the subgroup, and these coating enable processing of the subgroup of analytes such as concentrating and separating.

The concentrator may have phased heaters that heat in synchrony a volume element of a flow of fluid having analytes that moves by each phased heater, where each phased heater is turned on just long enough to desorb adsorbed analytes and to increase a concentration of the analytes in the volume element of the flow of fluid. In other words, each phased heater may turn off and decrease in temperature when the volume element of the fluid leaves the respective phased heater.

The pre-concentrator may have phased heaters that desorb analytes, previously adsorbed in the pre-concentrator, into a volume element of a flow of fluid that moves through the pre-concentrator by each phased heater which turns on just long enough while the volume element of a flow of fluid passes by each phased heater. The respective heaters may turn off and decrease in temperature when a certain portion of fluid leaves the each heater. The volume element of a flow of fluid may form a slug on analyte-concentrated sample gas that may be immediately ready to flow and interact with the downstream concentrator 823. Concentrator 823 may function similarly as the pre-concentrator.

From the concentrator 823, the gas slug, lump or pulse 830 may enter or be injected into the separator 824. There may be a wider window of heating in the separator (e.g., 1-3 seconds) than in either concentrator. There may be fast and slow gases moving through the separator (i.e., a basis of separation of the gases for analysis). There may be a gradual ramp increase of temperature in the separator up to about 250 degrees C. Thus, the slow gases may come through the separator at a higher temperature than the fast moving gases. The separator heating elements (e.g., phased heaters) may be switched off before the first fast analyte and after the slow gas or last analyte of interest passes the respective separator heating elements. Detection instrumentation may be situated upstream and downstream of the concentrator and the separator.

Micro analyzer 800, as shown in FIG. 25, may take in a sample stream of fluid 830 through an input 843 to a filter 827. From filter 827, fluid 830 may go into a first-level pre-concentrator 826 having series connected channels 829. However, the channels 829 may be connected in parallel or have a combination of series and parallel connections. From pre-concentrator 826, a first portion of fluid 830 may go through filter 831 and a second portion of fluid 830 may go through concentrator 823, having at least one channel 32 with phased heaters 20, 22, 24, . . . , 26, within or proximate to the channel and adsorber coated interactive elements 40, 42, 44, . . . , 46 proximate to the heaters, and a flow sensor/micro-detector 832. Concentrator 823 may also have a channel 31 with interactive elements 140, 142, 144, . . . , 146 proximate to phased heaters 40, 42, 44, . . . , 46. Fluid 830 may be drawn through channels 829 by pump 821. Surfaces, except for the adsorber coated surfaces, inside the channel or channels of concentrator 823 may be coated with an insulative coating 69 (FIGS. 6a, 6b and 6c). Pump 822 may draw fluid 830 through the main portion of micro analyzer 800 including concentrator 823, sensor/detector 832 and separator 824. Pumps 821 and 822 may operate simultaneously or according to individual schedules. From sensor/detector 832, fluid 830 may also go through a second micro detector 833, second separator 825 and a third micro detector 834. Fluid 830 may be pulled forth by pump 822.

The concentrators 826 and 823, and separators 824 and 825 may have columns with temperatures of up to 300° C. which may consume energy rapidly and limit the time of operation and/or raise the size of the smallest battery that can be used in analyzer 800 in a normal application. Several approaches may be used to reduce this high energy demand. Relative to the separators 824 and 825, one may reduce the energy needed to ramp up the temperature of the separator column, by only raising the temperature of the active parts of the column. This may be accomplished with a segmented column by switching off the heaters that are located behind in time and location of the tail-end of the last analyte to elute within the scheduled analysis time. In other words, one may reduce energy consumption per analysis by shutting off heat to separator 824 and 825 elements located behind the last compound peak to elute within the allotted total elution time period.

As to the pre-concentrator 826, energy savings may accrue from not heating at once the whole first-level concentrator (i.e., pre-concentrator 826) but only the last pre-concentrator element associated with the high-analyte-concentration fluid plug to be fed to the second-level concentrator (i.e., concentrator 823), and by fabricating the pre-concentrator 826 with adsorber films as thick as possible but yet still compatible with the needed desorption speed, to minimize the resulting β (vol. gas/stat.phase ratio) and flow restrictions.

Figure 27:
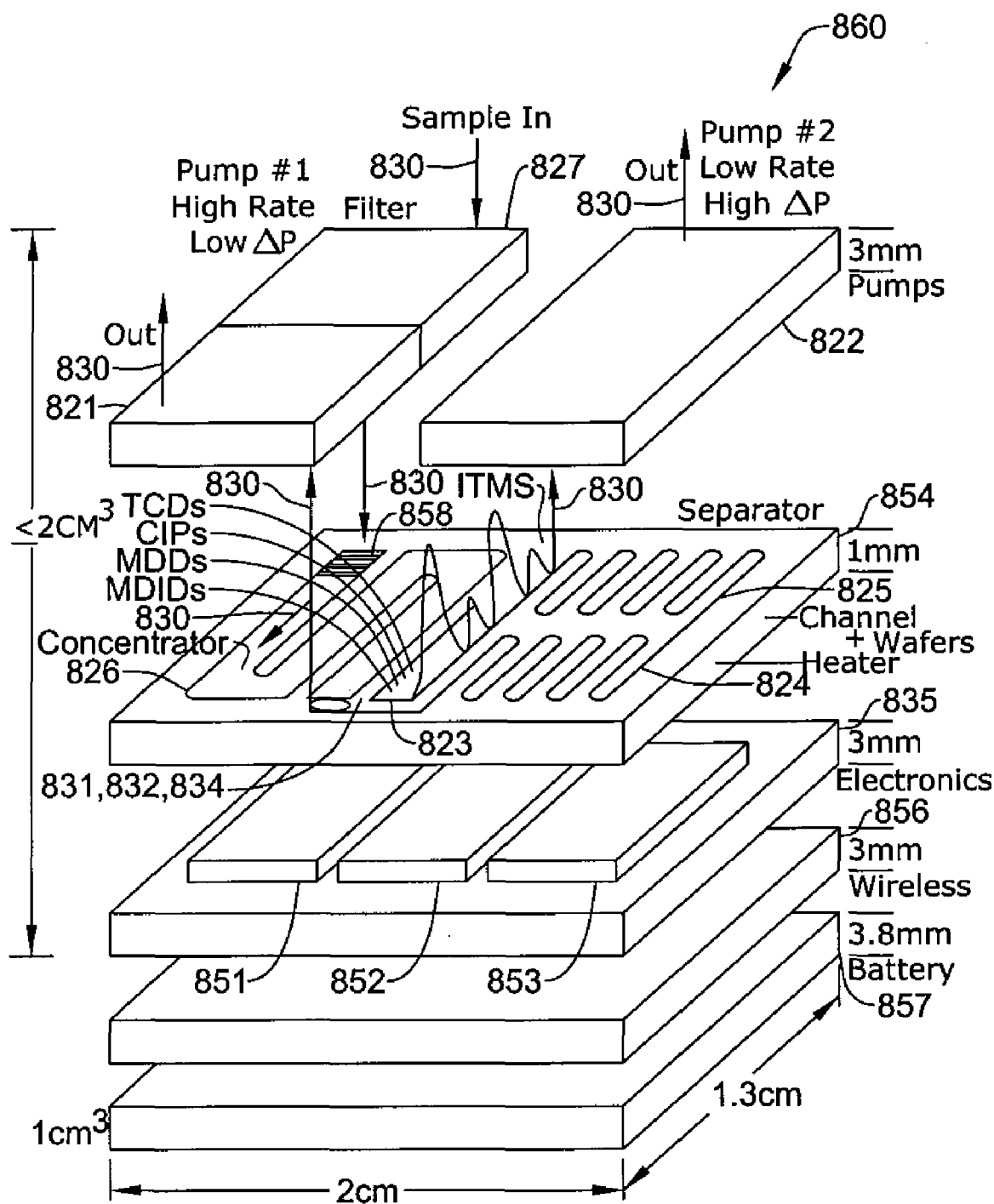
FIG. 27 is an expanded perspective view of the low power, low volume micro analyzer.

Energy saving features may include allowing an increase in the width of the pre-concentrator channel 829 to accommodate the needed adsorber film mass needed to achieve the needed total concentration gain (~total gain×injector vol./100); allowing increased adsorber film thickness in the pre-concentrator 826 to reduce its overall size, reduce the flow restriction and pressure drop, and increase pre-concentrator 826 gain by decreasing the vol. gas/stat.phase ratio, β, and segmenting the wide pre-concentrator 826 elements and energize each of them only for enough time to desorb the adsorbed analytes. The illustrative example of FIG. 27 shows a hint of the associated segmentation of the 5-mm-wide first-level concentrator 826 into 50 to 200 micron-wide heater strips 858 at right angles to the direction of flow of fluid 830 along its total length of 20 millimeters. The heater strips may constitute phased heaters. The heater elements of the pre-concentrator may form an array of narrow parallel strips having a longitudinal dimension equal to the width of the flow channel and a narrow dimension parallel to the direction of flow of the analyte sample of 10-100 times smaller than the width of the channel.

Fluid 830 exiting from pumps 821 and 822 may be returned to the place that the fluid was initially drawn or to another place. Each of micro detectors 831, 833 and 834 may include a TCD, MDD, PID, CRD, CID, ITMS, MS, and/or other kinds of detectors or instrumentation. However, there might be only a TCD and CID at micro-detectors 832 and 833. Analyzer 800 may have more or fewer detectors than those shown. The detectors may have a thin film material including polymeric material, metal oxide and nanotube structure material. Some of the detectors may detect absolute and differential resistance changes. The polymeric material may be able to indicate concentration of analyte based on changes in electrical resistance, capacitance, adsorbed mass or mechanical stress. It may also have flow orifices, such as orifices 841 and 842 at the outlets of micro detectors 833 and 834, respectively. Analyzer 800 may also have valves and other components at locations where advantageous. A control device 835 or micro controller or processor may be connected to pumps 821 and 822, detectors or sensors 831, 832, 833 and 834, pre-concentrator 826, concentrator 823, separators 824 and 825, and other components as necessary to adequately control and coordinate the operation of analyzer 800. Analyzer 800 may have structural similarities relative to other micro fluid analyzers described in the present description.

The use of multiple detectors may increase analyzer 800 reliability in terms of minimizing the occurrence of false identification analytes, leading to "false positives", either with or without a mass spectrometer. As to detector choices, one may add more than the TCD instrumentation to the analyzer 800 in order to increase analyte identification reliability and thus reduce the probability of false positives, as discussed herein. This string of PC, CS and detectors may have the format of either PC(1+2)+CS(1+2)+TCD+CID+MDID+ITMS or

PC(1+2)+CS(1+2)+TCD+CID+MDID+PID+MDD.

CID may designate a chemical impedance detector (chemi-resistor or -capacitor) and MDD may designate a micro discharge device. Types of mass spectrometers may include quadrupole, time-of-flight and magnetic deflection.

Figure 25A:
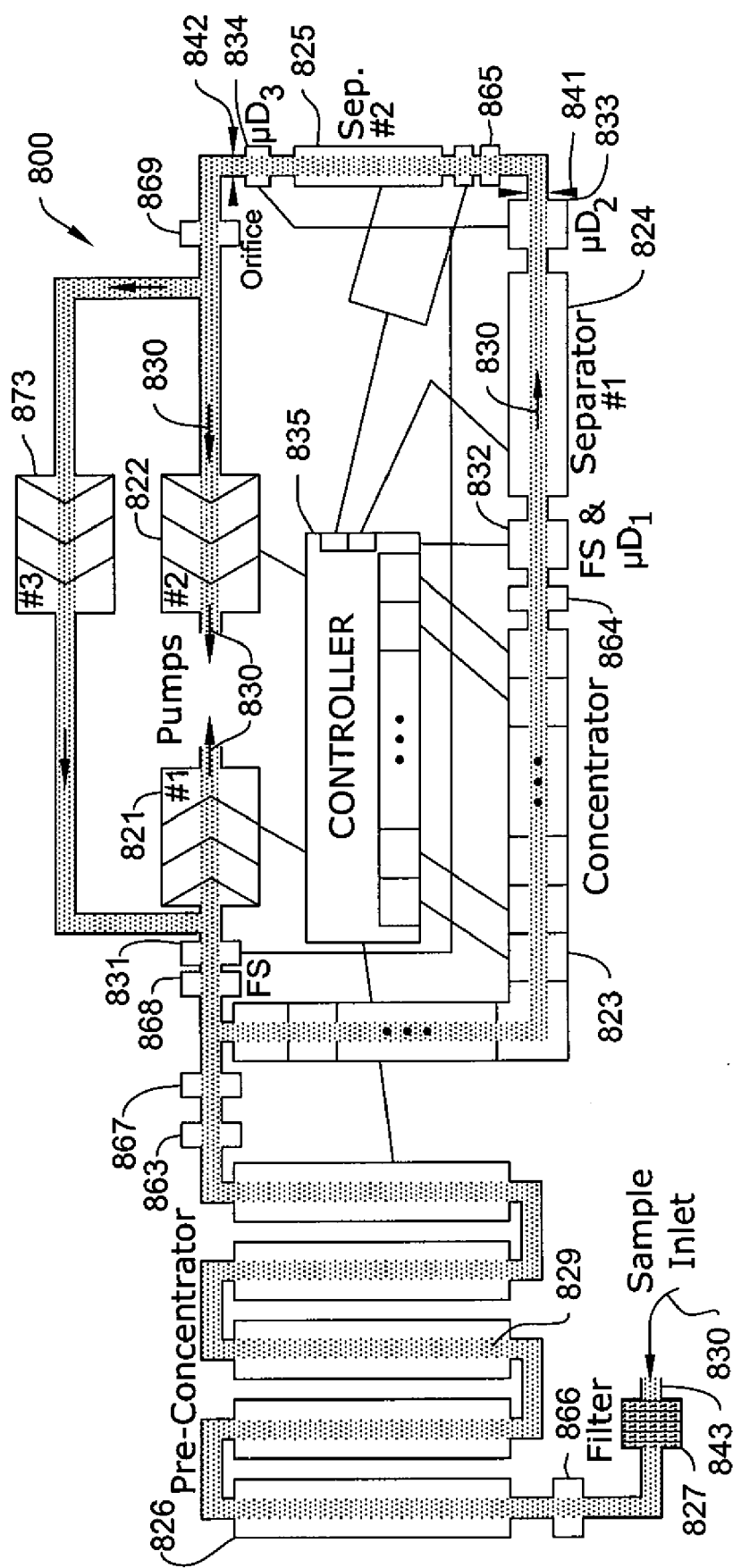
Figure 26A:
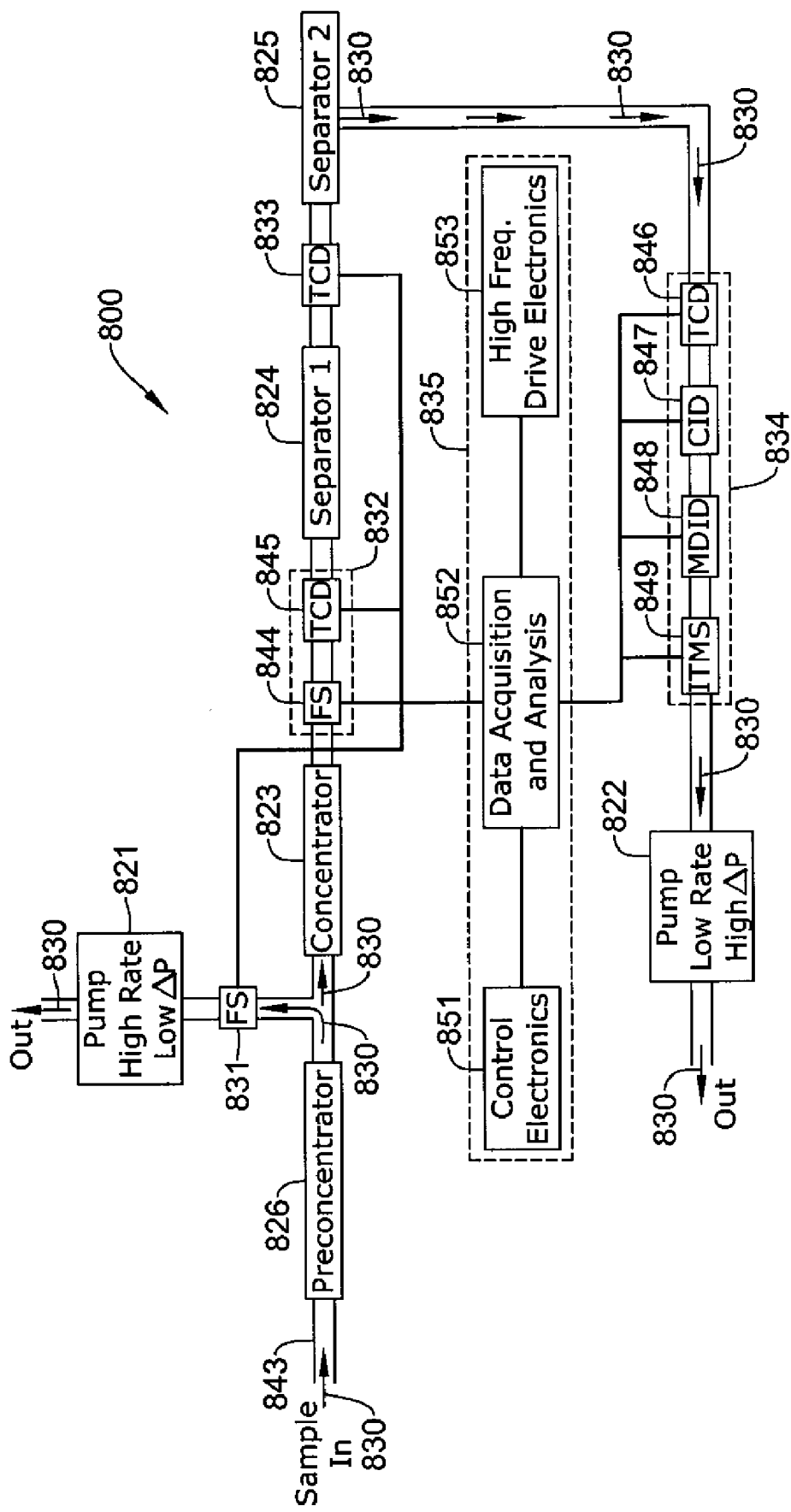
FIGS. 26a, 26b and 26c are flow diagrams of a low power, low volume micro analyzer.
Figure 26B:
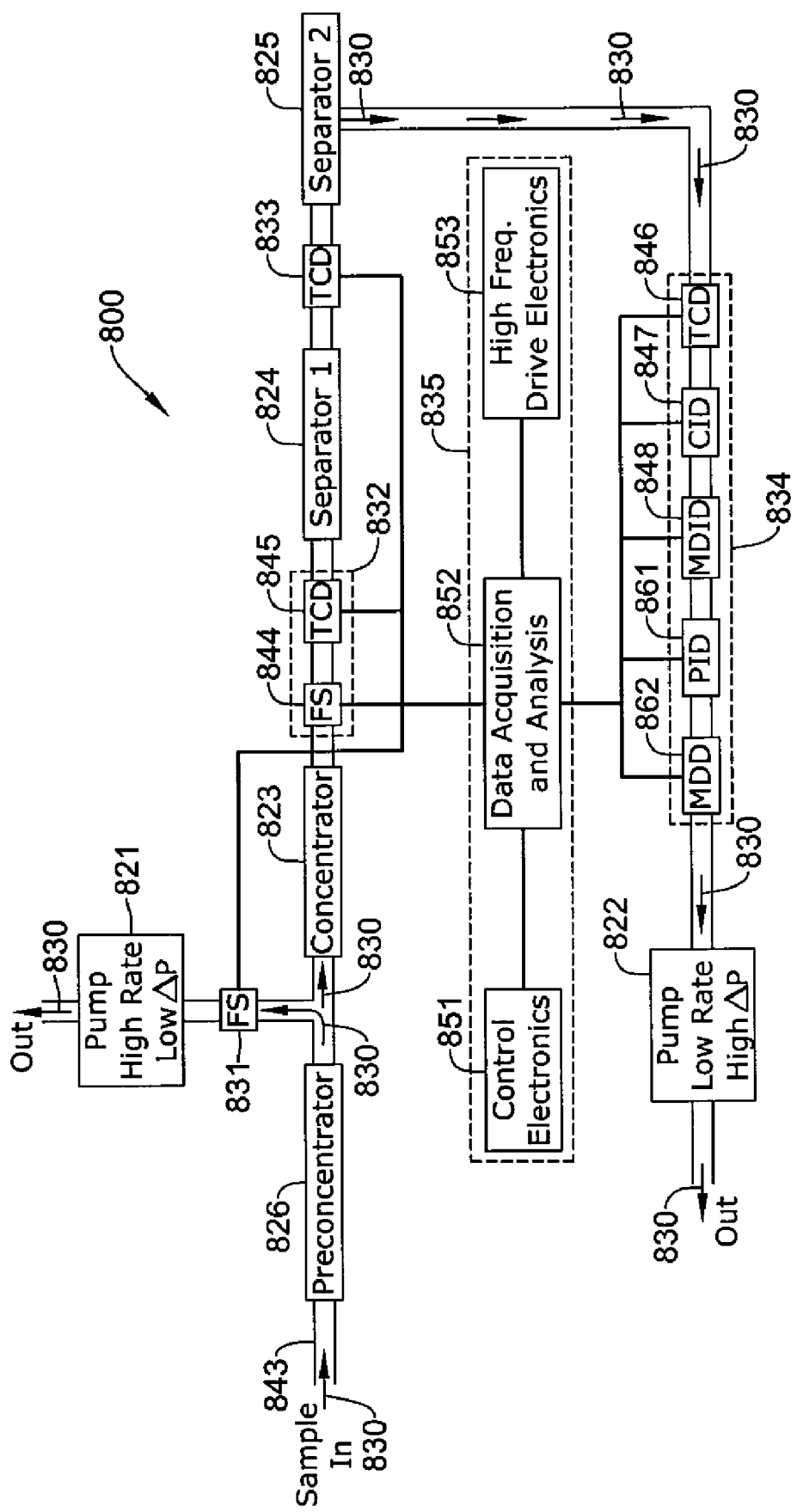
Figure 26C:
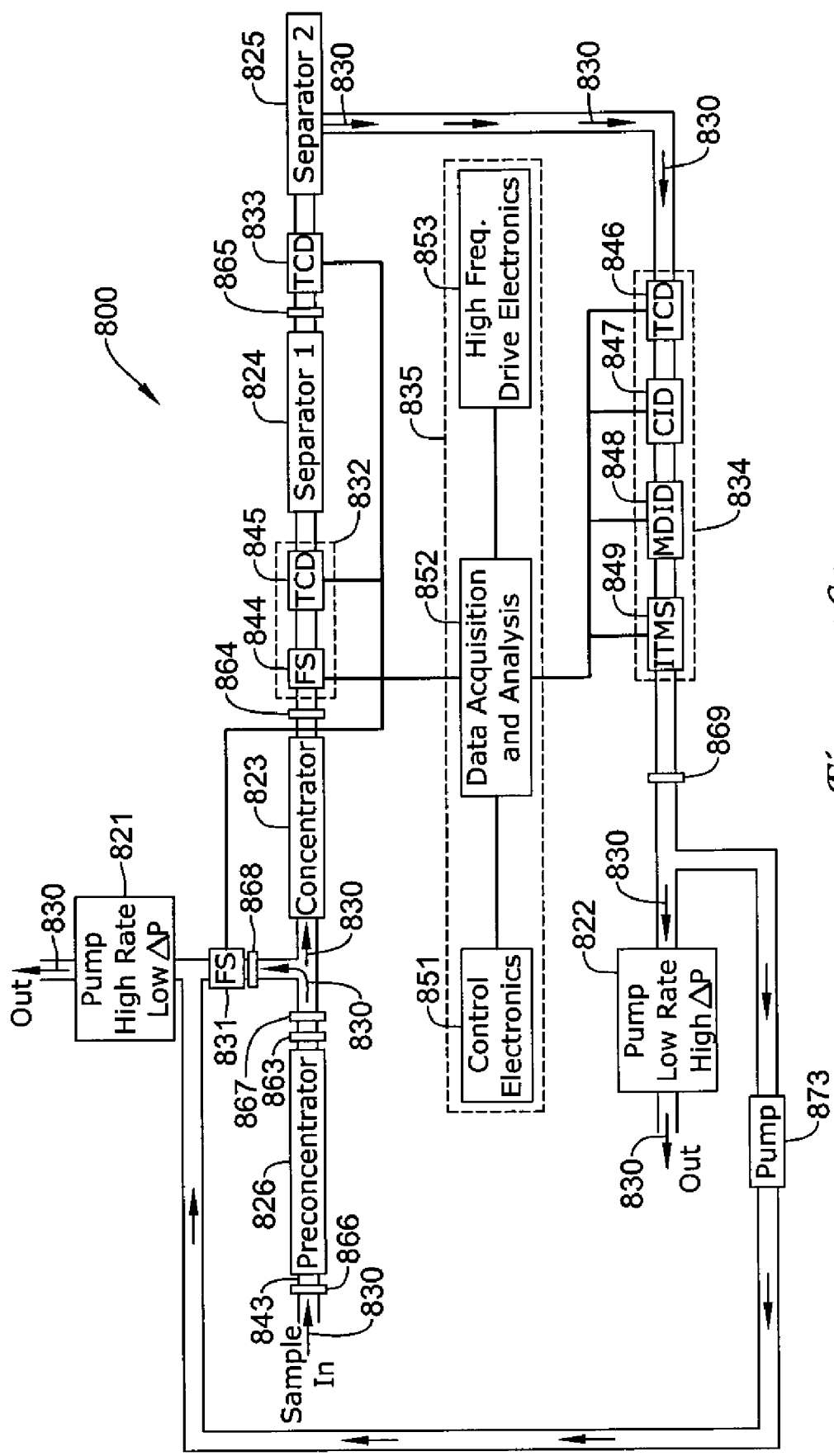

FIG. 26a is a flow diagram of a modular phased micro analyzer 800 having two-level concentration. This diagram represents a similar configuration of FIG. 25 of analyzer 800. The diagram shows sample fluid entering an inlet 843 to pre-concentrator 826. The fluid 830 may split after pre-concentrator 826 to flow to integrated flow sensor 831 and concentrator 823, respectively. Fluid 830 may be pumped from sensor 831 through a high rate low delta pressure pump 821 to an exit from the analyzer 800 system. The fluid 830 going through concentrator 823 may go on to instrumentation 832 which may contain integrated flow sensor 844 and TCD 845. From instrumentation 832, fluid 830 may go through the first separator 824 and TCD 833. Then fluid 830 may go the second separator 825 and instrumentation 834. Instrumentation 834 may contain a TCD 846, CID 847, MDID 848 and ITMS 849. In FIG. 26b, PID 861 and MDD 862 may be connected to instrumentation 832 in lieu of ITMS 849 or in combination. MDD 849 may include versions having optical spectral emission of UV, visible and IR bandwidths. There may be additional MDDs for facilitating the measurement of various wavelength bands (each with its own narrow band-pass filter. Instrumentation 834 may contain more or less devices. The may be other kinds of devices in instrumentation 834. For instance, instrumentation 832, 833 and/or 834 may be thin-film polymers have capable of sensing passing analytes in the flow 830 via a film change in resistance, capacitance or stress and may change from about one micron to one nanometer (as self-assembled monolayer or otherwise) in thickness. There may be temperature sensors 863, 864 and 865 situated after pre-concentrator 826, concentrator 823 and separator 824, respectively, as shown in FIGS. 25a and 26c. These sensors 863, 864 and 865 may be connected to controller 835. From instrumentation 834, fluid 830 may be pumped out of analyzer 800 by a low rate high delta pressure pump 822. All sensors and detectors, including pumps, concentrators, separators, emission devices, spectrometers, and other devices may be connected to controller 835. Components may be interchanged from one version or example of analyzer 800 with another.

In FIGS. 25a and 26c, there may be pressure and/or differential pressure sensors 866 at the input of pre-concentrator 826, 867 at the outlet of pre-concentrator 826, 868 at the input of pump 821, and 869 at the input of pump 822. The pressure sensors provide information to sense flow by the first pump 821, which may be flow rate-adjusted via its actuator frequency, to sense the (first and second) separator flow rate of the second pump 822 and to sense vacuum for the mass spectrometer. There may be a third pump 873 having an inlet and outlet upstream of the second pump 822, which in turn may pump its output into the inlet of the high-flow-rate first pump 821.

In FIG. 26a, information from flow sensors 831 and 844, thermoconductivity detectors 845, 833 and 846, chemical impedance detector 847, micro discharge impedance detector 848 and ion trap mass spectrometer 849 may go to controller 835 for analysis of the information about fluid 830. The spectrometer may indicate molecular mass of the fluid 830. In FIG. 26b, information from flow sensors 831 and 844, thermoconductivity detectors 845, 833 and 846, chemical impedance detector 847, micro discharge impedance detector 848, photo ionization detector 861 and micro discharge device 862 may go to controller 835 for analysis of the information about fluid 830.

Controller 835 of FIG. 26a may include control electronics 851, a data acquisition and analysis module 852, and high frequency drive electronics 853. Controller 835 and other portions of analyzer may be incorporated in ASICs (application-specific integrated circuits). Module 852 may be connected to flow sensor 844, TCD 833, 845 and 846, CID 847, MDID 848 and ITMS 849. Also, module 852 may be connected to control electronics 851 and high frequency drive electronics 853. Pre-concentrator 826, concentrator 823, first separator 824, second separator 825, first pump 821 and second pump 822 may be connected to controller 835 (shown in FIG. 25). FIG. 26*b* shows ITMS 849 replaced with PID 861 and MDD 862 which may be connected to module 852.

FIG. 27 shows an expanded perspective of micro analyzer 800. The lateral dimensions of the package or module 860 of the analyzer may be about 2 cm by 1.3 cm. Module 860 may be a stack of wafers or chips. The vertical dimension of the package may be about 0.7 cm for a volume of about 1.8 $cm^3$. The lower portion of the module 860 may be controller 835 that contains a control electronics 851 chip, a data acquisition and analysis 852 chip and a high frequency drive electronics 853 chip. The lower portion may have a thickness of about 3 millimeters. A middle portion 854 may include pre-concentrator 826, concentrator 823, first separator 824, second separator 825, instrumentation 831, 832 and 834, and at least one channel and the phased heaters 20, 22, 24, . . . , 26. Portion or wafer 854 may or may not include the ITMS 849. Spectrometer 849 may be on a separate chip or stack of chips. The middle portion 854 may have a thickness of about one millimeter. The top portion may contain the first pump 821, second pump 822 and filter 827. The top portion may have a thickness of about 3 millimeters. At the bottom of the lower portion of module 860 may be a layer or portion 856 of wireless communication electronics for data transfer and control of micro analyzer 800. This layer 856 may have a thickness of about 3 millimeters and have about the same lateral area as that of the module 860. Below layer 856 may be a portion for a battery 857 or power pack or holder having a thickness of about 3.8 millimeters thick and about the same lateral area as that of module 860. The battery 857 may be thicker (e.g., 10 millimeters) or thinner depending on the power needed for the analyzer 800, the desired time between recharges and the technology (e.g., lithium) of the battery. If all of the portions, including the wireless electronics and the battery, are adhered together, the total thickness may be about 1.38 centimeters resulting in a volume of about 3.6 $cm^3$. The dimensions may be relaxed if exceptional compactness is not needed. In the latter case, the top portion with the pumps may have an area less than 25 square centimeters and a thickness less than 10 millimeters. The portion 856 for wireless communication may have an area less than 25 square centimeters and a thickness less than 10 millimeters. The lower portion with controller 835 may have an area less than 25 square centimeters and a thickness of less than 10 millimeters. The middle portion 854 may have an area less than 25 square centimeters and a thickness less than 10 millimeters. The portion for the battery 857 or its holder may have an area less than 25 square centimeters. The above dimensions may be alternatively less than 2.5 square centimeters in lieu of 25 square centimeters.

Although the invention has been described with respect to at least one illustrative embodiment, many variations and modifications will become apparent to those skilled in the art upon reading the present specification. It is therefore the intention that the appended claims be interpreted as broadly as possible in view of the prior art to include all such variations and modifications.

What is claimed is:

1. A fluid analyzer comprising:
   means for concentrating the group of analytes with phased heaters;
   means for separating the group of analytes; and
   means for measuring a differential thermal conductivity of the fluid before, between and after concentrating and separating certain analytes of the fluid.

2. The analyzer of claim 1, further comprising pre-concentrating the fluid prior to concentrating the fluid.

3. The analyzer of claim 1, wherein:
   adsorber coatings are formed on the phased heaters;
   the adsorber coatings comprise two or more compositions;
   each adsorber coating adsorbs a subgroup of the group of analytes and lacks interaction with the analytes not in the subgroup; and
   the subgroup of analytes is concentrated and separated.

4. The analyzer of claim 1, further comprising means detecting absolute and differential resistance changes before and after separating certain analytes of the fluid.

5. The analyzer of claim 4, wherein the means for detecting comprises a material from a group consisting of polymeric material, metal oxide and nanotube structure material.

6. The analyzer of claim 5, further comprising means for measuring voltage, current and optical spectral emission bands of a micro discharge device exposed to the group of analytes before and after separating the group of analytes.

7. The analyzer of claim 6, further comprising:
   a means for measuring molecular masses of analytes of the group of analytes after separating the group of analytes; and
   wherein the means for measuring molecular masses is a mass spectrometer.

8. The analyzer of claim 7, wherein the mass spectrometer is selected from a group consisting of ion trap, time of flight, magnetic deflection and quadrupole type of mass spectrometers.

9. The analyzer of claim 7, further comprising:
   means for analyzing the group of analytes with information; and
   wherein the information is from the means for measuring a differential thermal conductivity of the fluid before, between and after concentrating and separating certain analytes of the fluid, means detecting absolute and differential resistance changes before and after separating certain analytes of the fluid, means for measuring voltage, current and optical spectral emission bands of a micro discharge device exposed to the group of analytes, and a means for measuring molecular masses of analytes of the group of analytes.

* * * * *